US007084265B1

(12) United States Patent
Ayabe et al.

(10) Patent No.: US 7,084,265 B1
(45) Date of Patent: Aug. 1, 2006

(54) POLYNUCLEOTIDE ENCODING 2-HYDROXYISOFLAVANONE SYNTHASE

(75) Inventors: Shinichi Ayabe, Yamato (JP); Toshio Aoki, Sagamihara (JP); Tomoyoshi Akashi, Yamato (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 09/890,646

(22) PCT Filed: Feb. 4, 2000

(86) PCT No.: PCT/JP00/00596

§ 371 (c)(1),
(2), (4) Date: Aug. 2, 2001

(87) PCT Pub. No.: WO00/46356

PCT Pub. Date: Aug. 10, 2000

(30) Foreign Application Priority Data

Feb. 4, 1999 (JP) ................................. 11/063745

(51) Int. Cl.
C12N 15/29 (2006.01)
C12N 15/52 (2006.01)
C12N 15/74 (2006.01)
C12N 15/79 (2006.01)

(52) U.S. Cl. .................. 536/23.6; 536/23.2; 435/69.1; 435/320.1

(58) Field of Classification Search ................ 800/278, 800/298; 536/23.1, 23.2, 23.6; 435/419, 435/430, 468, 183, 320.1, 243, 69.1, 70.1, 435/71.1
See application file for complete search history.

(56) References Cited

FOREIGN PATENT DOCUMENTS

WO        00/44909       8/2000

OTHER PUBLICATIONS

Akashi T. et al. Nov. 19, 1996; GenBank Accession No. D89436.*
Fourgoux-Nicol et al 1999, Plant Molecular Biology 40:857-872.*
Steele C. et al. Archives of Biochemistry and Biophysics; Jul. 1, 1999; vol. 367, No. 1; pp. 146-150.*
GenBank accession No. AF135484 submitted Mar. 17, 1999.*
GenBank Accession No. AF022462 submitted on Sep. 4, 1997.*
GenBank Accession No. D89436, submitted on Nov. 20, 1996.*
Napoli C. et al. Plant Cell; Apr. 1990; vol. 2; pp. 279-289.*
Otani K. et al. Plant Physilogy, 1994, vol. 105; pp. 1427-1432.*
Broun P. et al. Science vol. 282; Nov. 13, 1998, pp. 1315-1317.*
Liu C. et al. The Plant Journal, 2003; vol. 36 pp. 471-484.*
Sawada Y. et al. The Plant Journal, 2002; vol. 31 No. 5; pp. 555-564.*
Siminszky, B. et al. GenBank Accession AF022462 made public on Jan. 2, 1998.*
Akashi, T. et al.; "Cloning and Functional Expression of a Cytochrome P450 cDNA Encoding 2-Hydroxyisoflavanone Synthase Involved in Biosynthesis of the Isofavonoid Skeleton in Licorice"; *Plant Physiology*; vol. 121, pp. 821-828; 1999.
Hakamatsuka, T. et al.; "Purification of 2-Hydroxyisoflavanone Dehydratase from the Cell Cultures of *Pueraria lobata*"; *Phytochemistry*; vol. 49, No. 2, pp. 497-505; 1998.
Kochs, G. et al.; "Enzymic Synthesis of Isoflavones"; *Eur J. Biochem.*; vol. 155, pp. 311-318; 1986.
Hashim, M. F. et al.; "Reaction Mechanism of Oxidative Rearrangement of Flavanone in Isoflavone Biosynthesis"; *FEBS Letters.*; vol. 271, No. 1,2, pp. 219-222; 1990.
Meijer, A. H. et al.; "Isolation of Cytochrome P-450 cDNA Clones from the Higher Plant *Catharanthus roseus* by a PCR Strategy"; *Plant Molecular Biology*, vol. 22, pp. 379-383; 1993.
Akashi, T. et al.; "Cloning of Cytochrome P450 cDNAs from Cultured *Glycyrrhiza echinata* L. Cells and Their Transcriptional Activation by Elicitor-Treatment"; *Plant Science*; vol. 126, pp. 39-47; 1997.
Akashi, T. et al.; "CYP81E1, a Cytochrome P450 cDNA of Licorice (*Glycyrrhiza echinata* L.), Encodes Isoflavone 2'-Hydroxylase"; *Biochemical and Biophysical Research Communications*; vol. 251, pp. 67-70; 1998.
Akashi, T. et al.; "Identification of a Cytochrome P450 cDNA Encoding (2S)-Flavanone 2-hydroxylase of Licorice (*Glycyrrhiza echinata* L.; Fabaceae) which Represents Licodione Synthase and Flavone Synthase II"; *FEBS Letters*; vol. 431, pp. 287-290; 1998.
Schopfer, C. R. et al.; Molecular Characterization and Functional Expression of Dihydroxypterocarpan 6a-Hydroxylase, an Enzyme Specific for Pterocarpanoid Phytoalexin Biosynthesis in Soybean (*Glycine max* L.); *FEBS Letters*, vol. 432, pp. 182-186; 1998.

(Continued)

*Primary Examiner*—Russell P. Kallis
(74) *Attorney, Agent, or Firm*—Oliff & Berridge, PLC.

(57) ABSTRACT

2-Hydroxyisoflavanone synthase substantially having the amino acid sequence represented by SEQ ID NO:2 and a polynucleotide substantially having the nucleotide sequence of SEQ ID NO:1. Thus, 2-hydroxyisoflavanone synthase can be expressed in a host cell. By transferring the polynucleotide encoding 2-hydroxyisoflavanone synthase into a plant cell, a plant having an altered isoflavone productivity can be obtained.

14 Claims, 11 Drawing Sheets

OTHER PUBLICATIONS

Akashi, T. et al.; Two New Cytochrome P450 cDNAs (Accession Nos. AB001379 and AB001380 from Elicitor-Induced Licorice (*Glycyrrhiza echinata* L.) Cells (PGR97-167); *Plant Physiol*, vol. 115, pp. 1288; 1997.

Steele, C. L. et al.; Molecular Characterization of the Enzyme Catalyzing the Aryl Migration Reaction of Isoflavonoid Biosynthesis in Soybean; *Archives of Biochemistry and Biophysics*; vol. 367, No. 1, pp. 146-150; 1999.

Dixon, R. A. et al.; "Flavonoids and Isoflavonoids—A Gold Mine for Metabolic Engineering"; *Trends in Plant Science*; vol. 4, No. 10, pp. 394-400; 1999.

\* cited by examiner

Liq: Liquiritigenin

Liq: Liquiritigenin
Dai: Daidzein

1),3) CYP Ge-8

2),4) pYES2 (CONTROL)

Time after YE-treatment (h)

(A) pBI121
(B) pBIGe-8S8
(C) pBIGe-8A4

(A)  (B)  (C)  (D)

M:1Kb Ladder (1)  (2)  (3)

M: 1Kb Ladder
P: pBIGe-8S8
C: Control

POLYNUCLEOTIDE ENCODING 2-HYDROXYISOFLAVANONE SYNTHASE

TECHNICAL FIELD

The present invention relates to a polynucleotide containing a newly identified nucleotide sequence encoding 2-hydroxyisoflavanone synthase, and the transformant transformed with the polynucleotide.

BACKGROUND ART

Isoflavones are compounds having an isoflavone skeleton which are contained predominantly in leguminous plants. It is known that isoflavones will act as a phytoalexin in plants. A phytoalexin is an antibacterial substance which plants produce against stresses such as microorganism infection.

Moreover, isoflavones, especially daidzein and genistein are physiologically active substances having an estrogen-like activity, which are notable for an effect of preventing breast cancer or osteoporosis. Moreover, there are also substances which attract attention as powerful antioxidation substances, such as 6,7,4'-trihydroxy isoflavone, 7,8,4'-trihydroxy isoflavone and the like. On the other hand, there was a case that a problem of sterilization of livestock arose when leguminous plants which are rich in isoflavones were used as food for livestock. Therefore, there have been noted the possibility of control of an amount of isoflavones produced in plants for the purpose of improvement in disease resistance of plants and production of isoflavones suitable as feed for livestock or the like. An isoflavone skeleton is biosynthesized via oxidative aryl migration from flavanones to 2-hydroxyisoflavanones, as shown in FIG. 1, and it is known that an enzyme catalyzing the reaction, i.e., 2-hydroxyisoflavanone synthase, exists. Therefore, 2-hydroxyisoflavanone synthase is a very important enzyme in synthesis of isoflavones.

Although isolation and purification of 2-hydroxyisoflavanone synthase, and elucidation of the amino acid sequence of 2-hydroxyisoflavanone synthase and the DNA sequence encoding the amino acid sequence are important for production of isoflavones having the above-mentioned useful activity and control of the amount thereof produced in plants, isolation and purification of 2-hydroxyisoflavanone synthase and elucidation of the cDNA sequence have not been realized.

In order to isolate cDNA of 2-hydroxyisoflavanone synthase and to determine the DNA sequence and the amino acid sequence thereof, the inventors have studied plant materials, culture conditions, mRNA induction, and the like, and as a result, have succeeded in cloning the cDNA encoding 2-hydroxyisoflavanone synthase from the cDNA library produced from the cells obtained at 6 to 12 hours after elicitor treatment of the callus culture of a licorice (*Glycyrrhiza echinata*) with yeast extracts.

DISCLOSURE OF THE INVENTION

Polypeptide

The present invention relates to 2-hydroxyisoflavanone synthase having the amino acid sequence substantially comprising the amino acid sequence shown as SEQ-ID-No.:2.

Hereafter, "2-hydroxyisoflavanone synthase" is abbreviated to "IFS."

"Substantially comprising the amino acid sequence shown as SEQ-ID-No.:2" means that the amino acid sequence may include variation(s) such as deletions, substitutions, additions and insertions in the amino acid sequence. That is, IFS of the present invention may contain such variations, as long as the above-mentioned enzyme activity is maintained. The number of amino acids which are deleted, substituted, added or inserted may be, for example 1–20, preferably 1–10, and especially 1–5. For example, an amino acid residue can be replaced by a different amino acid residue with similar characteristics. The typical substitution may be a substitution between Ala, Val, Leu, and Ile, between Ser and Thr, between the acid residue Asp and Glu, between Asn and Gln, between the basic residues Lys and Arg, or between the aromatic residues Phe and Tyr.

Furthermore, the present invention also relates to a polypeptide having an antigen activity of the IFS set forth in claim 1.

Polynucleotide

The present invention relates to a nucleotide substantially comprising a nucleotide sequence encoding the above-mentioned 2-hydroxyisoflavanone synthase or a nucleotide sequence complementary thereto.

"A polynucleotide substantially comprising a nucleotide sequence encoding the above-mentioned 2-hydroxyisoflavanone synthase or a nucleotide sequence complementary thereto" includes: polynucleotides consisting of these nucleotide sequences and encoding the above-mentioned IFS, polynucleotides having different sequences therefrom due to degeneracy, polynucleotides to which suitable sequence(s) is added at 5'-end, 3'-end, or both of them depending on use.

Moreover, the present invention relates to a polynucleotide substantially comprising a nucleotide sequence which has 50% or more homology to the nucleotide sequence comprised in SEQ-ID-No.:1, and encodes IFS or the nucleotide sequence complementary thereto.

The word "the nucleotide sequence comprised in SEQ-ID-No.:1" means the nucleotide sequence of SEQ-ID-No.:1 or a part of the nucleotide sequence.

By the terminology "substantially comprising" is meant that not only a nucleotide sequence which has 50% or more of homology to the nucleotide sequence comprised in SEQ-ID-No.:1, and encodes IFS or the nucleotide sequence complementary thereto, but a sequence wherein an adequate sequence is added thereto at 5'-end or 3'-end or both of them is also included depending on the use thereof.

The above-mentioned homology is preferably 70% or more, more preferably 80% or more, still more preferably 90% or more, and especially 95% or more.

The present invention also relates to a polynucleotide which has 70% or more of homology to the nucleotide sequence of 144–1712 of SEQ-ID-No.:1 and encodes IFS and a polynucleotide having a complementary sequence to the nucleotide sequence.

Furthermore, the present invention relates to the polynucleotides which can be hybridized to at least a part of the polynucleotide having the nucleotide sequence of SEQ-ID-No.:1, the nucleotide sequence of 144–1712 of SEQ-ID-No.:1, or the nucleotide sequence complementary thereto under stringent conditions or under mild conditions.

These polynucleotides include, in addition to polynucleotides which can be hybridized to the polynucleotide having the nucleotide sequence of SEQ-ID-No.:1, the nucleotide sequence of 144–1712 of SEQ-ID-No.:1, or a nucleotide sequence complementary to these nucleotides and which encode IFS, under a stringent condition or a mild condition, the fragments of these polynucleotides which can function as a primer or a probe.

The mild hybridization conditions and the stringent hybridization conditions are described, for example, in Sambrook et. al, Molecular Cloning, A Laboratory Manual, 2nd. Vol. 1, pp. 1.101–104, and Cold Spring Harbor Laboratory Press, (1989).

Furthermore, the present invention also relates to a polynucleotide or cDNA encoding 2-hydroxyisoflavanone synthase obtained by cloning using a polynucleotide set forth in claim 6, 8 or 9 as a probe from the cDNA library produced from the cells 3–6 hours, preferably 1 to 12 hours, and especially 1 to 8 hours after elicitor treatment of the cells of licorice, preferably *Glycyrrhiza echinata*. The elicitor treatment is preferably performed using the yeast extract.

Probe and Primer

The present invention also relates to a polynucleotide which may function as a primer or a probe for a polynucleotide encoding IFS or cDNA of IFS (hereafter referred to as the primer or probe of the present invention). These may be polynucleotides having a homology of 50% or more, preferably 70%, still preferably 80%, further preferably 90% or more, and especially 95% or more to the nucleotide sequence contained in SEQ-ID-No.:1, or a nucleotide sequence complementary thereto, and having a nucleotide sequence which may function as the probe or primer of the polynucleotide encoding 2-hydroxyisoflavanone synthase.

Preferably, the primer or probe of the present invention is a polynucleotide having a homology of preferably 70% or more, more preferably 80% or more, still more preferably 90% or more, especially 95% or more to a nucleotide sequence consisting of at least 15 contiguous nucleotides in SEQ-ID-No.:1 or a nucleotide sequence complementary thereto.

Moreover, the primer or probe of the present invention may be a polynucleotide which can be hybridized to at least 15 contiguous nucleotides in SEQ-ID-No.:1 or a sequence complementary thereto under stringent conditions. For example, the primer or probe of the present invention may be a polynucleotide having at least 15 contiguous nucleotides in SEQ-ID-No.:1.

Polypeptide

The present invention also relates to IFS encoded by a nucleotide sequence having a homology of 70% or more to the nucleotide sequence of 144–1712 of SEQ-ID-No.:1, and encoding IFS, or encoded by a polynucleotide which can be hybridized to the polynucleotide having the nucleotide sequence of 144–1712 of SEQ-ID-No.:1 or a nucleotide sequence complementary to this under stringent conditions.

The Recombinant DNA and RNA

The present invention also relates to: (a) A recombinant DNA or RNA containing the expression system which may express in a host cell the polynucleotide substantially comprising the nucleotide sequence encoding IFS having the amino acid sequence substantially comprising the amino acid sequence SEQ-ID-No. 2 or a nucleotide sequence complementary thereto.

(b) A recombinant DNA or RNA containing the expression system which may express in a host cell a polynucleotide having a nucleotide sequence having a homology of 70% or more of the nucleotide sequence of 144–1712 of SEQ-ID-No.:1, and encoding IFS.

(c) A recombinant DNA or RNA containing an expression system which may express in a host cell a polynucleotide which can be hybridized to a polynucleotide having the nucleotide sequence of 144–1712 of SEQ-ID-No.:1 or a nucleotide sequence complementary thereto under stringent conditions, and encodes IFS;

(d) A recombinant DNA or RNA which contains the polynucleotide set forth in claim 4 connected to an appropriate regulation sequence so that it can be expressed in a sense direction and which can be introduced into a plant cell and transform it so that it may over-produce IFS.

(e) A recombinant DNA or RNA which contains the polynucleotide set forth in claim 7 connected to an appropriate regulation sequence so that it can be expressed in a sense direction and which can be introduced into a plant cell and transform it so that it may over-produce IFS.

(f) A recombinant DNA or RNA which contains the polynucleotide set forth in claim 4 connected to an appropriate regulation sequence so that it can be expressed in an antisense direction and which can be introduced into a plant cell and transform it so that production of IFS can be inhibited according to antisense inhibition.

(g) A recombinant DNA or RNA which contains the polynucleotide set forth in claim 6 connected to an appropriate regulation sequence so that it can be expressed in an antisense direction and which can be introduced into a plant cell and transform it so that production of IFS can be inhibited according to antisense inhibition.

Moreover, the present invention relates to a host cell containing one of the above-mentioned recombinant DNAs or RNAs of (a)–(e).

Furthermore, the present invention also relates to a method for producing 2-hydroxyisoflavanone synthase comprising culturing the host cell. The method for producing may further include a step of collecting the produced polypeptides.

Furthermore, the present invention relates to a transgenic plant obtained by transforming a plant so that an amount of the product of the enzyme reaction catalyzed by 2-hydroxyisoflavanone synthase or derivatives thereof may be altered or increased by introducing one of the above-mentioned recombinant DNAs or RNAs into a plant cell. This transgenic plant may be a plant which produces IFS in the natural status, or a plant which does not produce it in the natural status.

Furthermore, the present invention relates to a transgenic plant obtained by transforming a plant so that an amount of the product of the enzyme reaction catalyzed by 2-hydroxyisoflavanone synthase or derivatives thereof may be decreased by introducing one of the above-mentioned recombinant DNA or RNA (f) or (g) into a plant cell. This transgenic plant may be a plant which produces IFS in the natural status, for example a leguminous plant.

In the case of transforming plant which produce IFS in the natural status, transformation may be conducted so that the plant may not produce IFS or an amount of IFS produced can be increased or decreased. In the case of transforming plants which do not produce IFS in the natural status, transformation can be carried out so that the plant may produce IFS.

Moreover, the monoclonal antibody and a polyclonal antibody against the polypeptide of the present invention can be manufactured by a method well known in the art, and the present invention also relates to the antibodies.

BEST MODE FOR CARRYING OUT THE INVENTION

1. Definition

Figure 1:
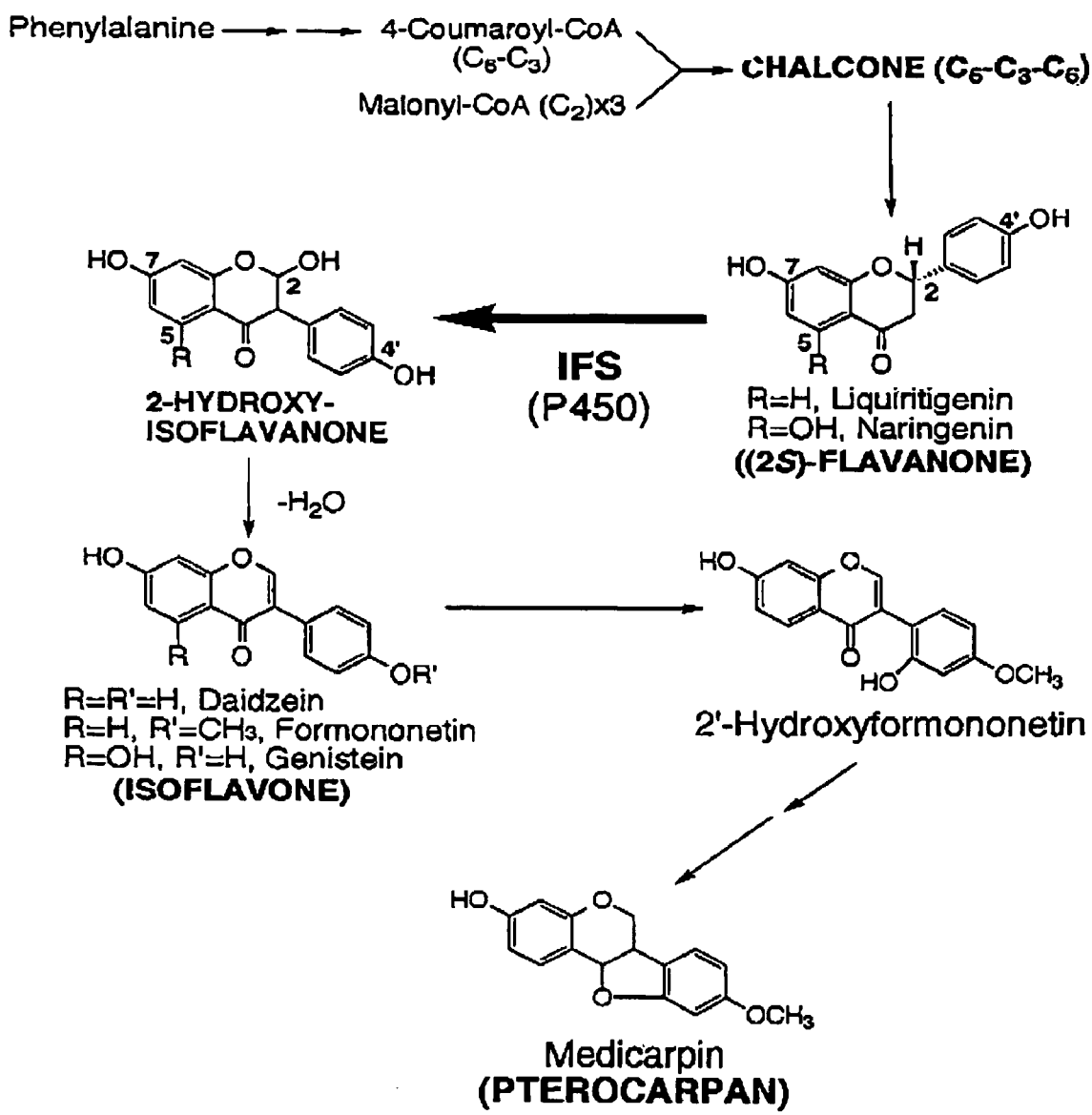
FIG. 1 is a reaction formula showing the reaction in which 2-hydroxyisoflavanone synthase of the present invention participates.

For easier understanding of the specification, a terminological definition will be shown below.

In the specification, "2-hydroxyisoflavanone synthase (hereafter referred to as IFS)" means a polypeptide having the enzyme activity of producing 2-hydroxyisoflavanon from flavanones as a substrate by a hydroxylation reaction and an aryl migration, in an analysis in a procedure usually used for analysis of the function of cytochrome P450.

Namely, it is meant that, for example, when the polypeptide is expressed in eucaryocytes, such as yeast, the microsome has the activity of catalyzing such a reaction under existence of a NADPH coenzyme or the like and under aerobic conditions, or is a polypeptide having the activity of catalyzing such a reaction under the above-mentioned condition when it is mixed with phosphatide such as P450 reductase and dilauryl phosphatidylcholine to reconstruct an electron transport system.

IFS of the present invention may be either isolated polypeptides which exist naturally, those produced by gene recombination technology, or those synthesized by known technology in the art.

Moreover, IFS of the present invention includes a polypeptide originated from *Glycyrrhiza echinata*, a polypeptide originated from other species belonging to *Glycyrrhiza* genus, a polypeptide originated form other genus belonging to a leguminous family, or a polypeptide originated from plants belonging to other families.

In this specification, "the polynucleotide of the present invention" may be polynucleotides set forth in any one of claims 2 to 9, and may be cDNA of IFS, and the polynucleotide encoding IFS, or a probe or a primer for obtaining the polynucleotide or the like.

The transformed *Escherichia coli* strain K12 CYP Ge-8 carrying the plasmid containing the polynucleotide encoding IFS of the present invention (cDNA of SEQ ID No.1) has been deposited with the Kogyo Gijutsuin Seimei-Kogaku Kogyo Gijutsu Kenkyujo of the Japan 1-1-3, Higashi, Tsukuba-shi, Ibaraki-ken on Feb. 1, 1999, and was accorded the accession number FERM P-17189, which was changed to deposition in accordance with the Budapest Treaty on the Deposition of Microorganisms on Jan. 31, 2000, and was accorded the accession number FERM BP-7010. The present invention also relates to a polynucleotide comprising nucleotide sequence encoding IFS obtained by a conventional method from of *Escherichia coli* strain K 12 of the accession number FERM BP-7010.

The "polynucleotide" includes poly ribonucleotides and poly deoxyribonucleotides, and may be unmodified RNA and DNA or modified RNA and DNA.

In the present invention, the "polynucleotide" may be those isolated from the naturally existing state.

Moreover, in the present specification, the term "polynucleotide" includes single strand DNA, double strand DNA, DNA comprising single strand part(s) and double strand part(s), single strand RNA, double strand RNA, RNA comprising single strand part(s) and double strand part(s), hybrid molecules containing DNA and RNA each of which may be single strand or double strand, or may comprise single strand part(s) and double strand part(s).

The word "polynucleotide" also includes DNA or RNA containing one or more modified nucleotides, and DNA or RNA having a skeleton modified for stability or other reasons.

The word "modified base" includes a tritylated base or a base like an inosine. Therefore, a "polynucleotide" may be a polynucleotide modified chemically, enzymatically, or metabolically.

In the present specification, the word "polynucleotide" may also include an oligonucleotide.

The word "polypeptide" means a peptide or protein containing two or more amino acids bonding each other through a peptide bond or a modified peptide bond. The word "polypeptide" means both a short chain (so-called peptide, an oligopeptide, or oligomer) and a long chain (protein).

The "polypeptide" includes an amino acid sequence modified by a natural process like posttranslational-modification processing, or by a chemical-modification method well known in the art. Such a modification is well known in the art. The modification can may take place in any place of the polypeptide including a peptide skeleton, an amino acid side chain, an amino terminus, and a carboxyl terminus.

A polypeptide may include many types of modification. The polypeptide may be branched as a result of ubiquitination, or may be cyclized with or without being branched. Modification may include: an acetylation, an acylation, ADP ribosylation, an amidation, covalent bonding with a flavin, covalent bonding with a heme part, nucleotide, or covalent bonding with a nucleotide inductor, covalent bonding with a lipid or a lipid inductor, covalent bonding with a phosphotidil inositol, formation of a cross linkage, cyclization, formation of a disulfide bond, demethylation, and formation of a cross linkage by a covalent bond, formation of a cystine, formation of a pyroglutamic acid, formylizing, a gamma carboxylation, glycosylation, GPI anchor formation, hydroxylation, iodine-izing, a methylation, myristoylation, oxidization, protein decomposition-processing, phospholylation, prenylation, racemization, selenoylation, sulfation, and amino acid addition to protein by transfer RNA such as argininization, and ubiquitination.

The word "antisense inhibition" means inhibiting expression of a target gene by antisense RNA which is complementary to all or a part of the target primary transcript product or mRNA, and inhibiting processing, movement, and/or translation of the target primary transcript product or mRNA. The antisense RNA may be complementary to any part, i.e., 5' non coding sequence, 3' non coding sequence, intron, or a coding sequence of a specific gene transcript product. In addition, the antisense RNA as used herein can include the domain of a ribozyme sequence which increases the effect of inhibiting gene expression by an antisense RNA.

"The suitable regulatory sequence" used in the present specification means a natural or chimeric nucleotide sequence which is located in an upstream (5'), an inside and/or a downstream (3') portion of the polynucleotide of the present invention, and controls expression of the polynucleotide of the present invention.

"3' non coding sequence" means the DNA sequence part of a gene including polyadenylation signal, and any other regulation signal which can affect processing of mRNA or gene expression. The polyadenylation signal is usually characterized by affecting addition of the polyadenylic-acid part to the 3'-end of a mRNA precursor.

"Plants" means photosynthetic organisms of both an eukaryotic organism and a prokaryotic organism.

Although the polynucleotide of the present invention is explained by various expressions in the present specification, it is intended that the polynucleotide of the present invention includes all the nucleotide sequences which can be obtained by one skilled in the art using a procedure known in the art based on the information on a cDNA sequence which has been elucidated by the present invention, and of which IFS activity can be confirmed, and also includes all the nucleotide sequences that are used as a probe or a primer based on the information in order to obtain IFS.

2. Production of Transformant, and Production of IFS

The transformant of the present invention is obtained by introducing the recombinant DNA or RNA of the present invention into a host suitable for an expression vector used when producing this recombinant DNA or RNA. The purified polynucleotide is inserted in the restriction enzyme part or multi-cloning site of a suitable vector to provide the recombinant DNA or RNA, and the host cell is transformed using the recombinant DNA or RNA concerned.

The vector DNA in which a DNA fragment is inserted will not be limited as far as it can be replicated in a host cell, for example, plasmid DNA, phage DNA, or the like. Examples of the plasmid DNA may include: plasmids pUC118 (manufactured by TAKARA SHUZO CO., LTD.) and pUC119 (manufactured by TAKARA SHUZO CO., LTD.), pBluescript SK (+) (manufactured by Stratagene), pGEM-T (manufactured by Promega), and the like. Examples of the phage DNA may include M13mp18, M13mp19 and the like.

The host will not be limited, as far as it can express the target gene, and both an eukaryotic cell and a prokaryotic cell can be used as the host, but an eukaryotic cell is used preferably. For example, there can be used bacteria such as *Escherichia coli* and *Bacillus subtilis*, yeast such as *Saccharomyces cerevisiae*, an insect cell, animal cells such as a COS cell, and a CHO cell and the like.

When using bacteria such as *Escherichia coli* as a host, the recombinant DNA or RNA of the present invention is preferably autonomously replicable in the host, and preferably has a constitution comprising a promoter, polynucleotide of the present invention and a transcription termination sequence. For example, *Escherichia coli* can be XL1-Blue (manufactured by Stratagene), JM109 (manufactured by TAKARA SHUZO CO., LTD.), or the like, and an expression vector can be, for example, pBTrp2 or the like. As the promoter, any promoter can be used as long as it can be expressed in hosts, such as *Escherichia coli*. For example, there can be used promoters originated from *Escherichia coli*, phages, or the like, such as a trp promoter, a lac promoter, PL promoter, and PR promoter. A transformation can be performed, for example, by the procedure of Hanahan [Techniques for Transformation of *E. coli* In DNA Cloning, vol. 1, Glover, D. M. (ed.) pp 109–136, and IRLPress (1985)].

When using yeast as a host, YEp13, YCp50 or the like can be used as an expression vector. As a promoter, gal 1 promoter, gal 10 promoter, or the like can be used, for example. As a method for introducing the recombinant DNA or RNA into yeast, there can be used, for example, the electroporation method (Methods. Enzymol., 194,182–187 (1990)), the spheroplast method (Proc. Natl. Acad. Sci. USA, 84, 1929–1933 (1978)), the acetic acid lithium method (J. Bacteriol., 153,163–168 (1983)) or the like.

When using an animal cell as a host, pcDNAI, pcDNAI/ Amp (invitrogen) or the like can be used as an expression vector. As method for introducing the recombinant DNA or RNA into an animal cell, an electroporation method, a calcium phosphate method, or the like can be used, for example.

In the case that plasmid DNA is used as a vector, for example, in order to insert EcoRI DNA fragment into plasmid DNA, the plasmid DNA is previously digested using the restriction enzyme EcoRI (manufactured by NEB). Subsequently, a DNA fragment and the digested vector DNA are mixed, which is then affected by T4DNA ligase (manufactured by TAKARA SHUZO CO., LTD.) to provide a recombinant DNA.

Screening of the above-mentioned transformant can be conducted by selecting a colony containing the targeted gene according to colony hybridization using a DNA fragment containing a part of the targeted gene as a probe or by PCR method using as a primer 5'-primer synthesized based on the nucleotide sequence of the target gene, and 3'-primer synthesized based on the nucleotide sequence of a complementary strand, and can choose a colony containing the target gene by the PCR method using these primers.

If the transformant carrying the recombinant DNA or RNA obtained as mentioned above is cultured, the polypeptide of the present invention can be produced. The usual solid-culture method is sufficient as a culturing method, but it is desirable to adopt a liquid culture method.

As a medium in which a transformant is cultured, there can be used a medium wherein one or more kinds of mineral salts such as potassium phosphate, magnesium sulfate and ferric chloride are added to one or more sorts of nitrogen sources chosen, for example, from a yeast extract, peptone, a meat extract, or the like, and if desired, a saccharine material, an antibiotic, a vitamin, or the like is added thereto. Moreover, IPTG or the like may be added to the medium to induce expression of a gene, if desired. pH of the medium is adjusted to 7.2–7.4 when culturing is initiated, and a general aeration spinner culture method, a shaking culture method or the like may be conducted at preferably 36–38° C., preferably around 37° C. for 14 to 20 hours.

After a culturing is terminated, IFS of the present invention can be extracted from the culture according to a general method for purifying protein. That is, after destroying a cell and carrying out solubilization of the IFS in the presence of a surfactant by a lysis treatment using enzymes, such as lysozyme, ultrasonic spallation treatment, grinding treatment, or the like, IFS is discharged from the cells. Subsequently, an insoluble substance is removed using filtration or a centrifugal separation to provide a rough polypeptide solution.

IFS can be further purified from the above-mentioned rough polypeptide solution by a general method for purifying protein using a suitable surfactant. For example, an ammonium sulfate salting-out method, ion exchange chromatography, hydrophobic chromatography, gel-filtration chromatography, affinity chromatography, electrophoresis, or the like can be conducted solely or in combination.

IFS obtained by the above-mentioned procedure can be used to synthesize 2-hydroxy isoflavanone according to a hydroxylation reaction and an aryl migration from flavanones as a substrate after forming a micelle in the presence of P450 reductase and a phosphatide such as dilauryl phosphatidylcholine. When a transformant is an eucaryocyte, a microsome obtained by crushing the cell obtained by culturing after a transformation and subjecting it to a centrifugal separation can be used to synthesize 2-hydroxy isoflavanone by the same reaction. The present invention also relates to use of the polynucleotide of the present invention for manufacture of a compound obtained by the reaction of the enzyme of the present invention or derivatives thereof. Examples of such compounds or derivatives thereof include: daidzein, genistein, 6,7,4'-trihydroxy isoflavone, 7,8,4'-trihydroxy isoflavone, formononetin, and 2'-hydroxy formononetin, medicarpin or the like.

3. Transgenic Plants

There can be obtained transgenic plants transformed so that IFS, a product of the enzyme reaction catalyzed by IFS or its derivatives may be produced by introducing the polynucleotide encoding IFS of the present invention with the transcription regulatory region which can express in a plant cell such as a suitable promoter, a terminator, or the like into a plant cell. Thereby, it is made possible to express IFS in plants which do not express IFS originally, and thereby the plants can be made to produce 2-hydroxy isoflavanones, which is the product of the reaction catalyzed thereby and the derivatives thereof. Examples of the isoflavones can be those listed above. Therefore, the present invention relates also to use of the polynucleotide for obtaining plants which produces these substances. Such a method is useful for raising disease resistance of the plants by making a plant that does not contain isoflavones originally express isoflavones, or for providing plants as foods which contains a large amount of isoflavones.

Examples of a transcription regulatory region which can be expressed in the plant cell include CaMV35SRNA promoter, a CaMV19SRNA promoter, a nopaline-synthesis enzyme promoter or the like expressed in the whole plants mentioned above, RubisCO small-subunit promoter expressed in green organizations, the promoter region of genes expressed in specific parts such as seeds, for example, napin and phaseolin, or the like. Moreover, terminators such as a nopaline-synthesis enzyme terminator and a RubisCO small-subunit 3'-end part may be connected with 3'-end.

Moreover, expression can be increased by introducing an enhancer into a promoter region. The "enhancer" is a DNA sequence which can raise promoter activity. The enhancer may be an original element of a promoter, or a different-species element inserted in order to improve the level and/or tissue specificity of the promoter. Examples of an enhancer include: an enhancer of a virus as found in 35S promoter (Odell et al., Plant Mol. Biol. (1988)10:263–272), an enhancer from an opine gene (Fromm et al., Plant Cell 1(1989):977–984), and any other enhancers which may increase transcription when located in the promoter connected so that it can act on the polynucleotide of the present invention. Thereby, the transgenic plants wherein the content of isoflavones is high can be obtained. Examples of isoflavones are listed above. Therefore, the present invention relates also to use of the polynucleotide of the present invention for providing plants wherein a production amount of isoflavones is increased. Such a procedure is useful to provide plants of which disease resistance was raised, and plants provided as food containing isoflavones in a large amount.

Furthermore, according to the present invention, the expression of IFS in plants can be controlled by anti sense inhibition. That is, expression of IFS can be inhibited by introducing into a plant cell the vector containing the antisense RNA of the polypeptide of the present invention with an expression-control sequence such as a promoter. Thereby, the transgenic plants containing no or a reduced amount of isoflavones can be obtained. Examples of isoflavones are listed above.

Therefore, the present invention also relates to use of a polynucleotide for obtaining plants wherein production of these substances is controlled. This procedure is useful, for example, to provide feed which does not cause sterilization of livestock.

Transgenic plants can be obtained by a procedure widely known in the art, for example, the *Agrobacterium* method, the particle gun method, the electroporation method, the PEG method, or the like, and a method of being suitable for a host cell is chosen.

An example of the *Agrobacterium* method is a method using a binary vector. The method comprises transfecting a plant with a vector containing T-DNA originated from the Ti plasmid origin, a replication origin which can act in a microorganism such as *Escherichia coli* and a marker gene for choosing the plant cell or the microbial cell carrying the vector, growing the seed harvested from the resultant plants, and selecting transformed plants wherein the vector was introduced using expression of the marker gene as an index. The transformed plants to be intended can be obtained by measuring IFS activity or selecting plants wherein content of isoflavones as a product of the reaction catalyzed by IFS or a derivative thereof is altered (Plant Physiol., 91 and 1212 (1989), WO 94/02620, Plant Mol. Biol., 9, 135 (1987), Bio/Technology, 6, 915 (1988)).

Moreover, the particle gun method is performed by a procedure described in the following reference: Pro. Natl.

Acad. Sci. USA, 86, 145 (1989), TIBTECH, 8, 145 (1990), Bio/Technology, 6, 923 (1988), Plant Physiol., 87, 671 (1988), Develop. Genetics, 11, 289 (1990), Plant cell Tissue & Organ Culture, 33, 227 (1993).

The electroporation method can be performed by a procedure described in the following reference: Plant Physiol., 99, 81 (1992), Plant Physiol., 84, 856 (1989), Plant Cell Reports, 10, 97 (1991).

EXAMPLE

The present invention will be further explained by the following Examples. Unless being indicated otherwise, all ratios and percentages are based on weight. These Examples are for illustration, and do not limit the present invention. The person skilled in the art can make various improvements and modifications using the description of the present invention and information known in the art.

1. Plant Materials and Culture Methods

A callus culture was established from leaves and petiole of *Glycyrrhiza echinata* (hereafter referred to as a licorice). The callus was grown on half-strength Murashige-Skoog's medium (solidified with 0.3% (w/v) of gellan gum) containing α-naphthalene acetic acid (1 mg/l) and an N6-benzyladenine (1 mg/l), under 12 hours light (6,000 luxs) and 12 hours dark cycle. The culture was suspended and cultured in MS medium to which 2,4-dichlorophenoxy acetic acid (0.1 mg/1) and the kinetin (1 mg/l) were added. The culture was subjected to elicitor treatment by adding 0.2% (w/v) of yeast extract (YE, manufactured by Difco). Then, the cultured cells were collected by vacuum filtration, frozen in liquid nitrogen immediately, and saved at −80° C.

2. cDNA Library and Screening

RNA having poly (A) was isolated from the cultured cells of the above-mentioned licorice 6 hours and 12 hours after the elicitor treatment, using Straight A's mRNA isolation system (manufactured by Novagen). The RNAs having poly (A) (2.5 μg each) were mixed, cDNAs corresponding thereto were prepared using the ZAP-cDNA Synthesis Kit (manufactured by Stratagene) to construct a cDNA library. Plaques (2×10$^5$) of the cDNA library were transferred on High-bond N+ membrane (manufactured by Amersham), and screened using as a probe a polynucleotide having a sequence of SEQ ID No.3 labeled with horseradish peroxidase (hereinafter referred to as HRP) using an ECL direct nucleic acid labeling system (manufactured by Amersham). The polynucleotide is one of fragments obtained from the cultured cells of the licorice 8 hours after the same elicitor treatment as the above-mentioned elicitor treatment by PCR (95° C. for 3 minutes, then 30 cycles of 95° C. for 1 minute, 45° C. for 1 minute and 72° C. for 2 minutes, and finally 72° C. for ten minutes) using as the primers the synthetic polynucleotides of: 5'-(T/C/A) TI(C/G) CITT(T/C) (G/A) GIIIIGGI (A/C) (G/C) I(A/C) G-3' (I is inosine) (SEQ ID No.: 8) and 5'-AATACGACTCACTATAG-3' (SEQ ID No.: 9). Hybridization was performed using ECL hybridization buffer containing 500 mM NaCl and 5% blocking reagent at 42° C. for six minutes. The membranes were washed twice with 1×SSC containing 0.4% SDS at 55° C. for 10 min and twice with 2×SSC at room temperature for 10 minutes. ECL detection reagent (manufactured by Amersham) was added to the membrane to detect HRP-labelled hybrid composite. The membrane was exposed to Kodak XAR-5 film for one minute. Possible clones were inserted into pBluescript SK(−) phagemids by in vivo excision according to the manufacturer's protocols. The length of the inserted cDNA was determined by PCR using T3 (5'-ATTAACCCTCAC-TAAAG-3' (SEQ ID No.: 10)) and T7 (5'-AATACGACT-CACTATAG-3' (SEQ ID No.: 9)) primers, and the complete nucleotide sequences of the clones which had a length of about 2000 bp were determined. One of them was cDNA having a sequence of SEQ ID No.:1, and identified to be IFS according to the following procedures (hereinafter the complete nucleotide sequence cDNA is referred to as CYP Ge-8).

3. Construction of Expression Vectors, Expression in Yeast Cells and Preparation in Microsomes The coding region of CYP Ge-8 was amplified by PCR using KOD polymerase, CYP Ge-8 cDNA clone as the template and the following sense primer (Ge-8S1, SEQ ID NO.:4) and antisense primer (Ge-8A1, SEQ ID No.:5). The sequences of the specific primers were as follows:

Ge-8S1: 5'-AAACAGGTACCATGTTGGTGGAACTTGC-3'

Ge-8A1: 5'-CGCGCGAATTCTTTACGACGAAAAGAGT-T-3'

The sense primer has a KpnI site (GGTACC) upstream of the initiation codon (ATG) and EcoRI site (GAATTC) downstream of the termination codon (TAA). The KpnI-EcoRI fragment of the PCR product was cloned into corresponding sites of pYES2 expression vector (manufactured by Invitrogen) having URA3 selection marker. The protease deficit yeast (*Saccharomyces cerevisiae*) BJ2168 strain (a;prc 1-407, prb 1-1122, pep 4-3, leu2, trp1, and ura3-52 manufactured by Nippon gene corporation) was transformed with the plasmid pYES Ge-8 thus obtained according to the acetic acid lithium method. The transformant was selected in culture medium containing 6.7 mg/ml of yeast nitrogen base without amino acids (manufactured by Difco), 20 mg/ml of glucose, 30 μg/ml of leucine, 20 μg/ml of tryptophan, and 5 mg/ml of casamino acid.

The transformed yeast was cultured in the above-mentioned liquid medium (25 ml) for 10 hours for the induction of P450 protein, and cells were collected by centrifugal separation (3,000×g). The cells were transferred to 1000 ml (40 times) of the YPGE medium which does not contain glucose (10 g/l yeast extract (manufactured by Difco), 10 g/l of bactopeptone (manufactured by Difco), 20 g/l of galactose, 3% (w/v) of ethanol, and 2 mg/l of hemin), and cultured for 24 hours and 36 hours. The collected yeast cells were suspended in 0.1 M potassium phosphate (pH 7.5) containing 10% sucrose and 14 mM of 2-mercaptoethanol with glass beads (diameter of 0.35 to 0.6 mm), and disrupted by a vigorous shaking using a vortex mixer for 10 min. They were subjected to centrifugation procedures of 10,000×g and 15,000×g for 10 minutes, and the obtained supernatant was applied to ultracentrifugation procedures of 160,000×g for 90 minutes to prepare the microsome. The yeast cell transformed with pYES2 was used as control.

4. Enzyme Assay a) Manufacture of a Substrate

As radio labelled substrate for enzyme assay, (2S)-[$^{14}$C] liquiritigenin (7,4'-dihydroxyflavanone) and (2S)-[$^{14}$C]naringenin (5,7,4'-trihydroxyflavanone) were prepared. (2S)-[$^{14}$C]liquiritigenin (7,4'-dihydroxyflavanone) was prepared by incubating malonyl-CoA and 4-cumaroyl CoA with the cell free extract of the licorice cultured cell 12 hours after elicitor treatment and NADPH at 30° C. for 3 hours.

Moreover, (2S)-[$^{14}$C]naringenin (5,7,4'-trihydroxyflavanone) was prepared by the same method as the above except that NADPH was not added.

The resulting (2S)-[$^{14}$C]liquiritigenin (hereinafter referred to as the labelled liquiritigenin) or (2S)-[$^{14}$C]naringenin (hereinafter referred to as the labelled naringenin) were purified with TLC (6.4 kBq/nmol each, 0.08 nmol).

b) Reaction with the Labelled Liquiritigenin

The labelled liquiritigenin purified above was dissolved in 30 µl of 2-methoxyethanol, added to 1 ml of the above yeast microsome, and was incubated in the presence of 1 mM NADPH at 30° C. for 2 hr.

After the reaction was terminated with 30 µl acetic acid, the ethyl acetate extract in the mixture was analyzed by TLC-radiochromatoscanner.

Figure 2:
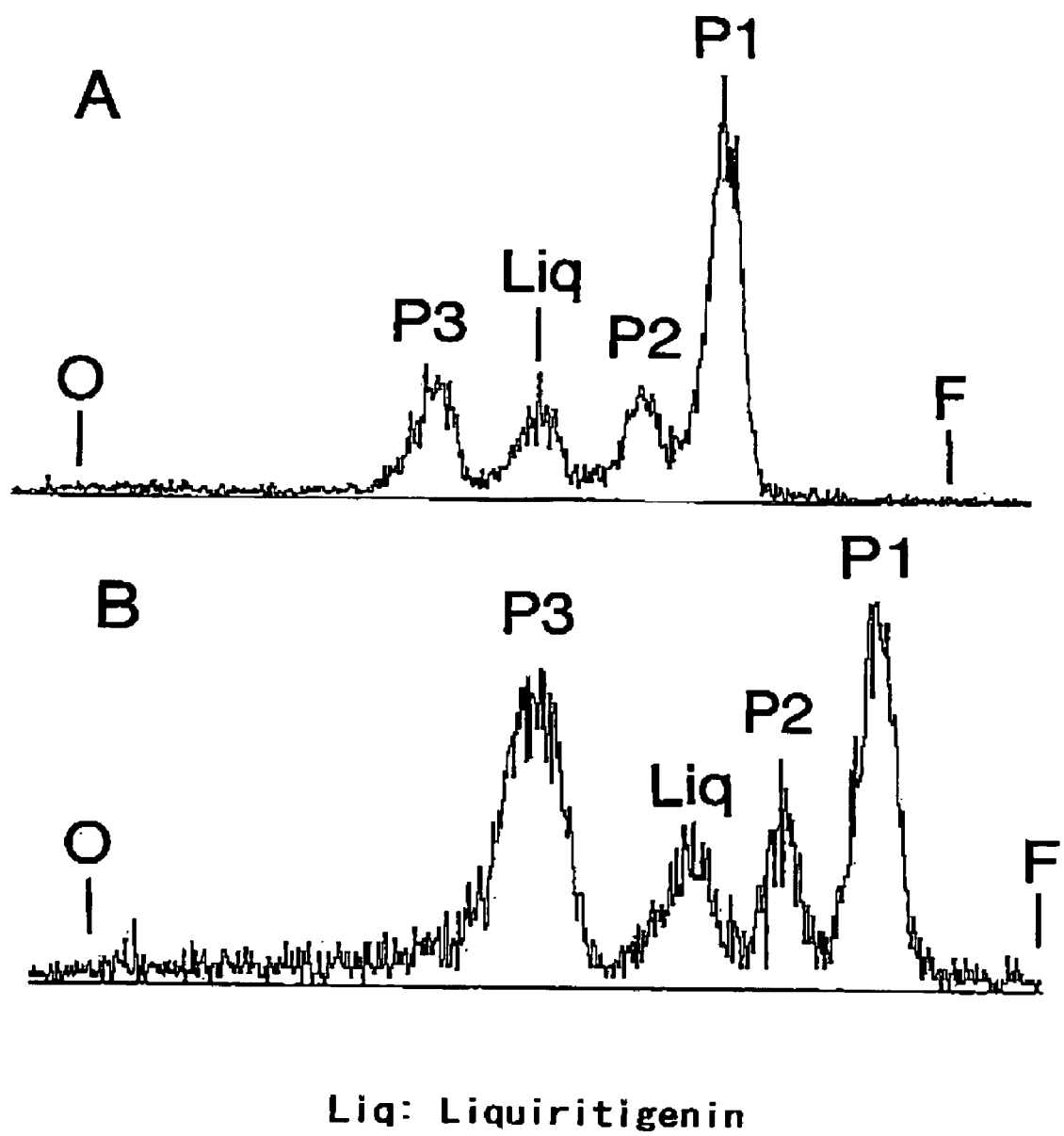
FIG. 2 is a chart showing the result of an enzyme assay of a yeast micro some transformed with the polynucleotide of the present invention.

TLC was developed with 15% acetic acid using the cellulose (manufactured by Funakoshi corporation, Funacel SF). The result is shown in FIG. 2A. From the chart, the existence of three radioactive compounds [P1 (Rf0.74), P2 (Rf0.64), P3 (Rf0.38)] other than an unreacted substrate (Rf0.51) was confirmed. From Rf value, P3 was determined with high possibility to be an isoflavone, namely daidzein (7,4'-dihydroxy) isoflavone.

For acid-catalyzed conversion of the reaction products into isoflavones, the concentrated ethyl acetate extracts were dissolved in 500 µl of 10% HCl in methanol, and stirred at room temperature for 1 h and 50° C. for 10 min. The reaction mixture was extracted with ethyl acetate, and the product was subjected to TLC under the same condition, and then analyzed by TLC radiochromatoscanner. The result is shown in FIG. 2B. As shown in the chart, the relative radioactivity at the Rf of P1 decreased and that of P3 increased.

Accordingly, P1 is highly possible to be 2,7,4'-trihydroxyisoflavanone, which should readily be dehydrated to give daidzein.

Figure 3:
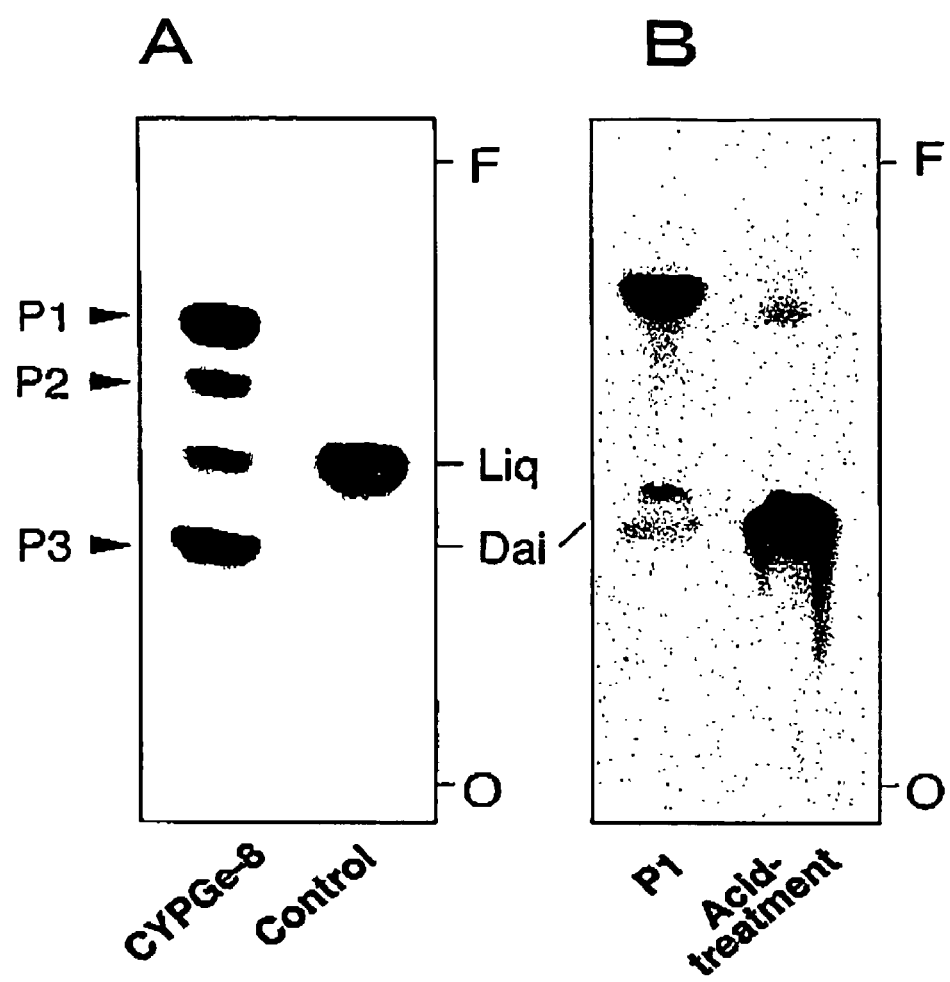
FIG. 3 is a photograph showing the result of an enzyme assay of a yeast micro some transformed with the polynucleotide of the present invention.

Furthermore, the radioactive P1 was isolated from the TLC plate of which autoradiogram was shown in FIG. 3A, reacted with HCl, and analyzed by TLC autoradiography. Thereby, a pure radioactive product P3 (daidzein) was produced as shown in FIG. 3B.

Figure 4:
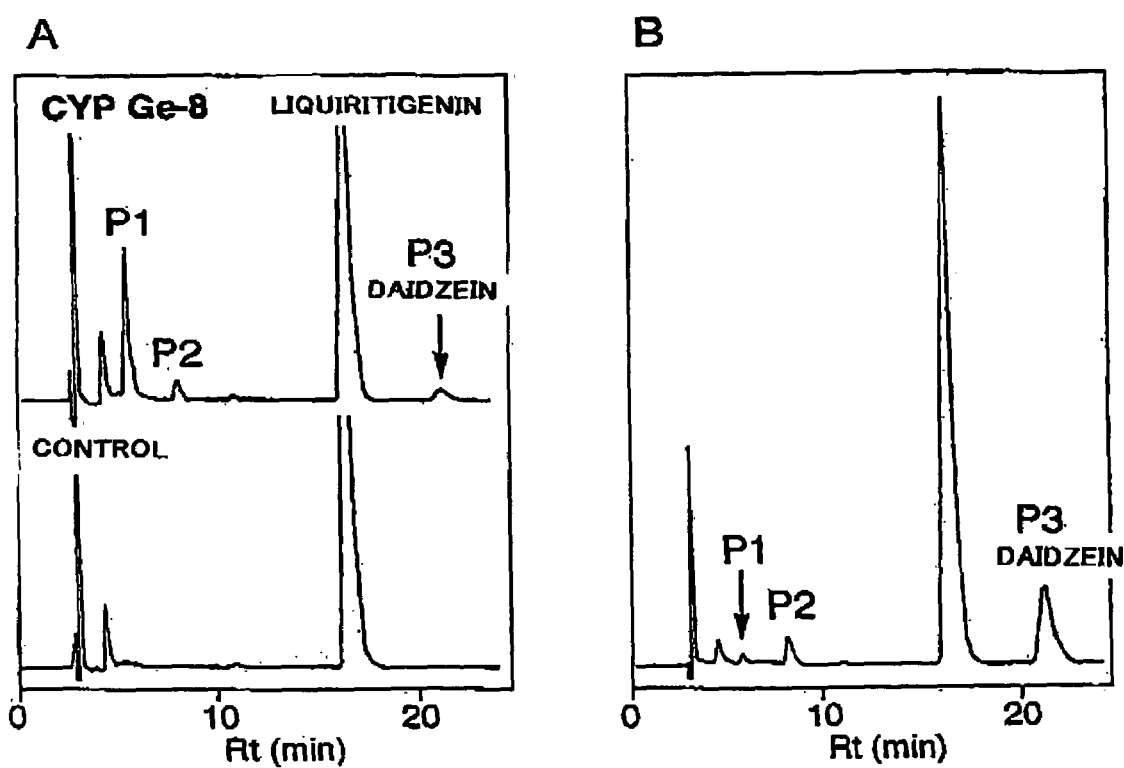
FIG. 4 is a chart showing the result of an enzyme assay of a yeast microsome transformed with the polynucleotide of the present invention.
Figure 5:
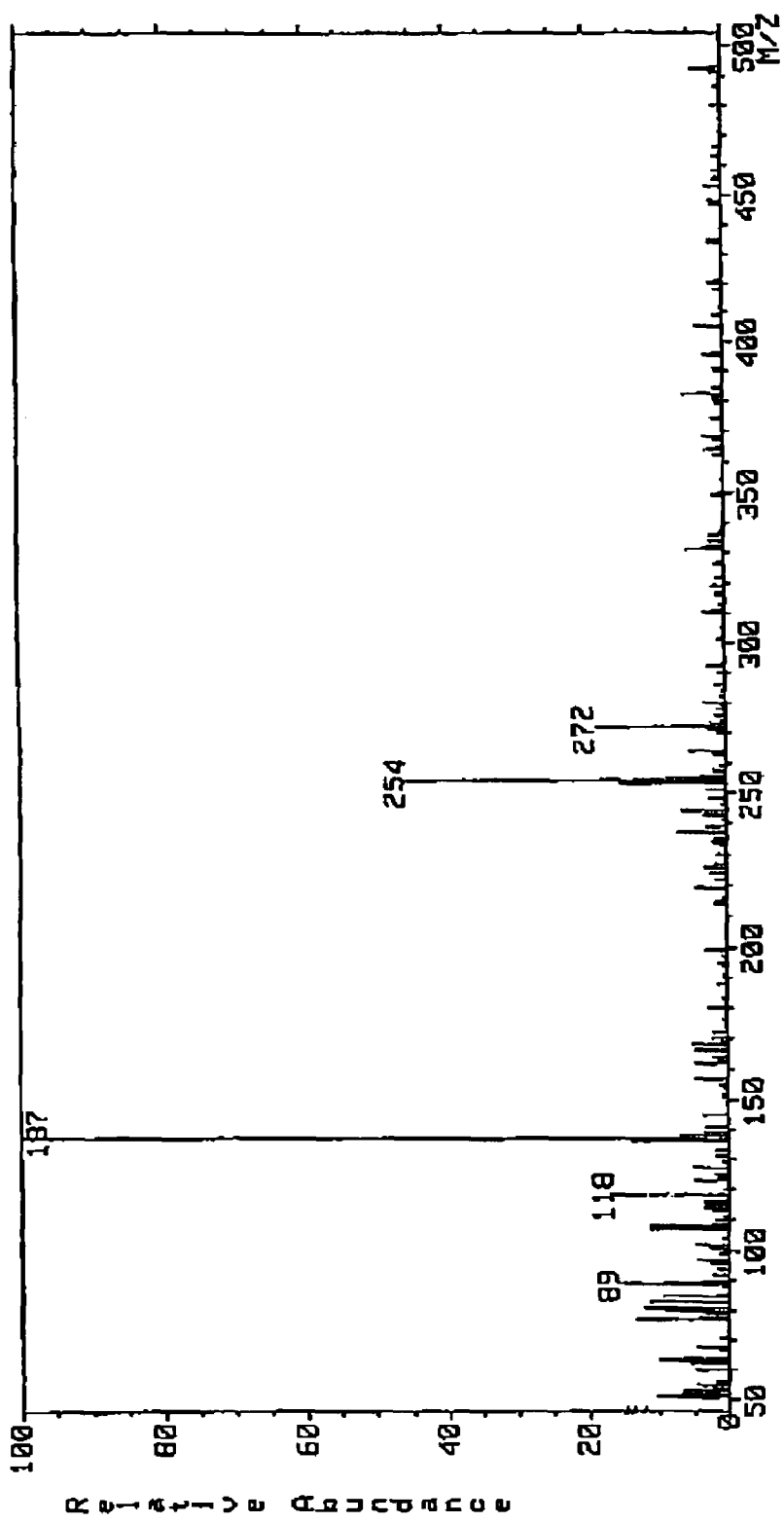
FIG. 5 is a chart showing the result of mass-spectrum analysis of the reaction product produced by the yeast microsome transformed with the polynucleotide of the present invention.
Figure 6:
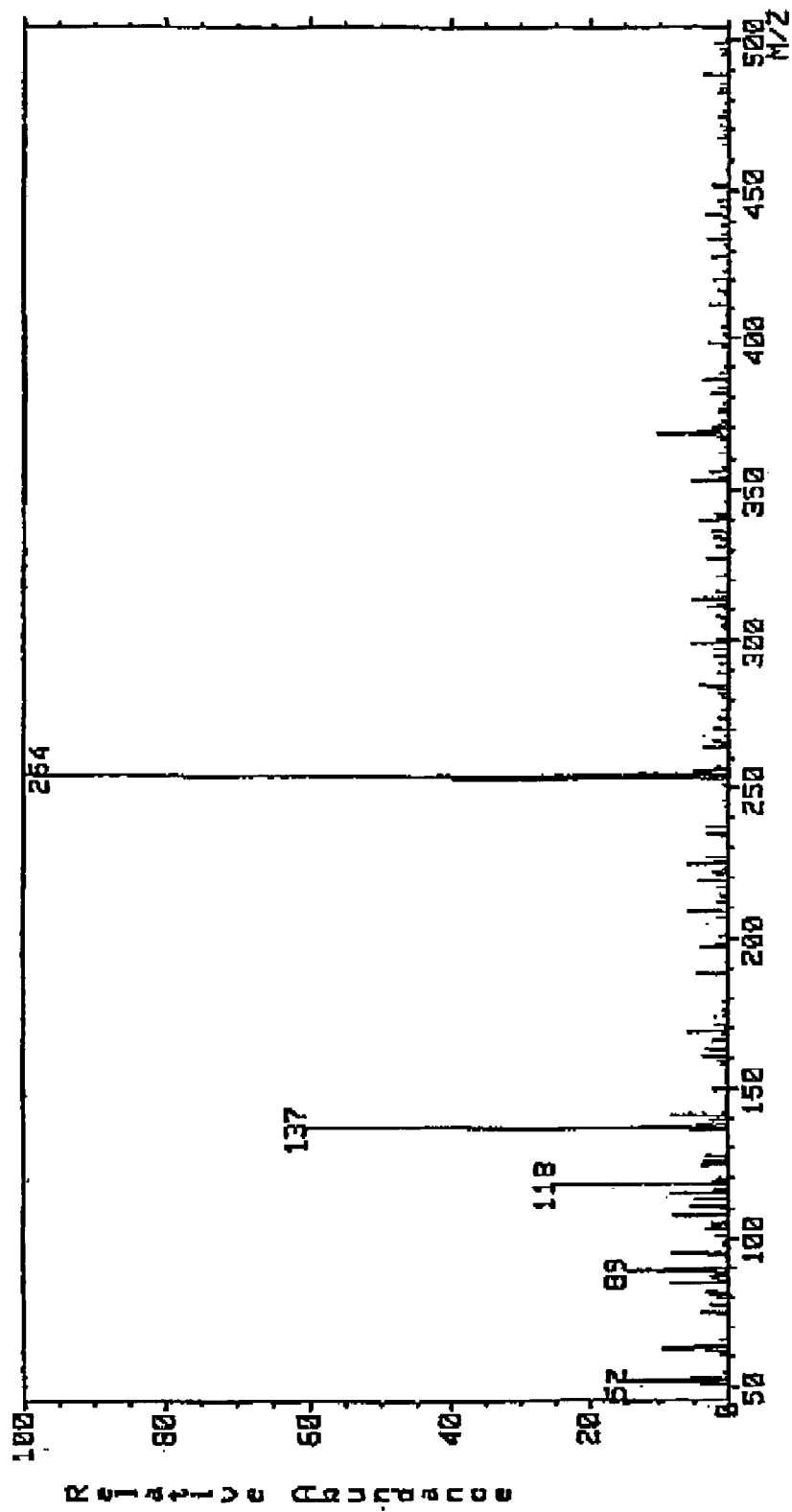
FIG. 6 is a chart showing the result of mass-spectrun analysis of the reaction product produced by the yeast microsome transformed with the polynucleotide of the present invention.

To further confirm that CYP Ge-8 is IFS, 10 µg of liquiritigenin without radiolabel was added to one ml of the above microsome and incubated at 30° C. for 2 hours in the presence of 1 mM of NADPH. The reaction mixture was extracted with ethyl acetate, and the ethyl acetate phase was analyzed by HPLC using a Shim-pack CLC-ODS column (6.0×150 mm; manufactured by Shimadzu) with 40% methanol in H$_2$O. The eluent was monitored at 285 nm. The result was shown in FIG. 4A. As expected, a peak of daidzein (Rt 21.0 min) and two additional peaks (Rt 5.5 and 7.9 min) were observed. When the ethyl acetate extract was treated with acid, an intense daidzein peak was observed as shown in FIG. 4B. The product giving Rt 5.5 min peak in FIG. 4A was proven to be P1 by TLC analysis.

For mass spectrometric analysis, the incubation of the above yeast microsome with liquiritigenin was carried out in a large scale (×200 of the scale described above). The ethyl acetate extract of the reaction mixture was applied to TLC for separation on Kieselgel F254 (manufactured by Merck) using as solvent toluene/ethyl acetate/methanol/petroleum benzine (6:4:1:3). The spots at the P1 (Rf0.2) and P3 (Rf0.3) spots were collected and further purified by HPLC. The mass spectra were recorded on a JEOL JMS-AX505H mass spectrometer under the electron impact (EI) mode with the ionization voltage of 70 eV.

c) Reaction with Labeled Naringenin

Figure 7:
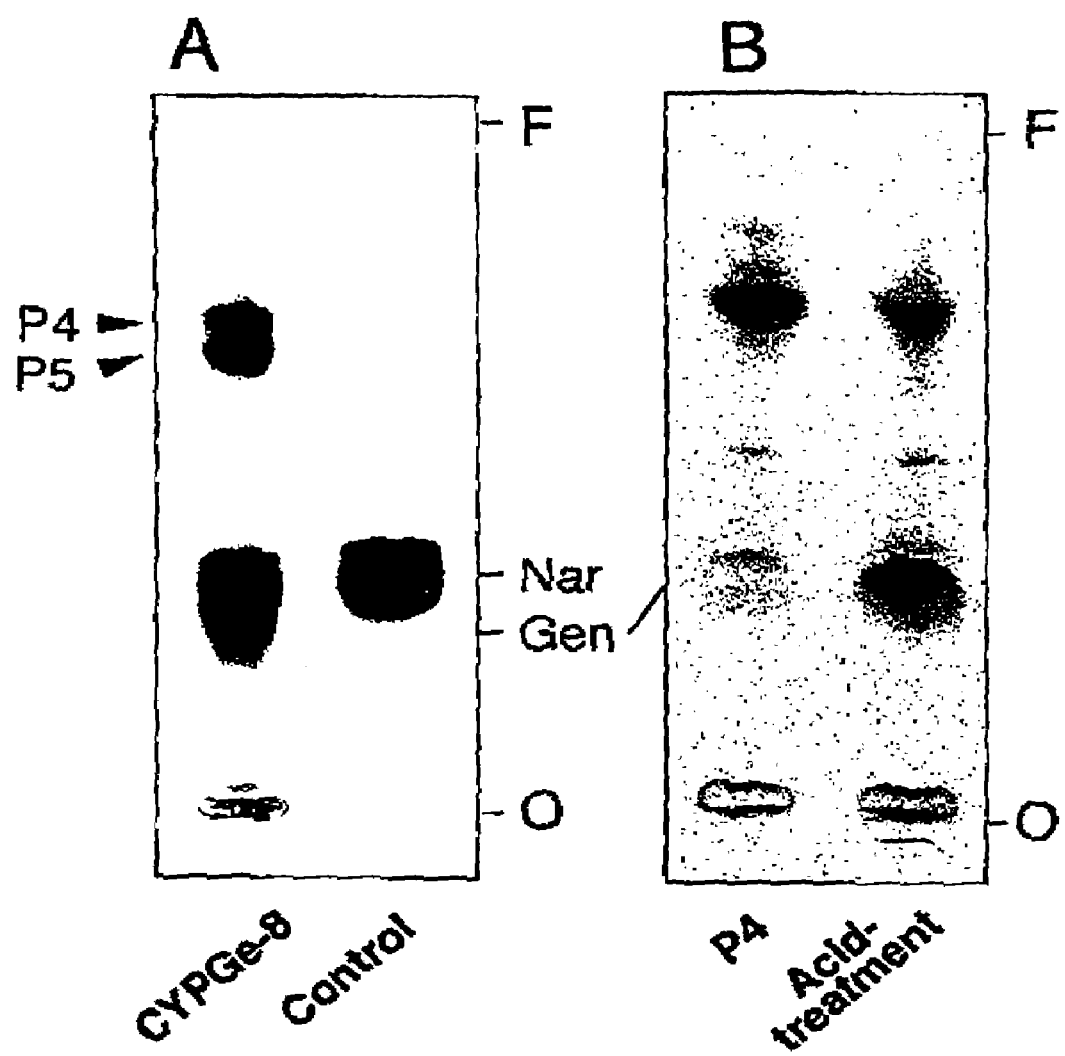
FIG. 7 is a photograph showing the result of an enzyme assay of the yeast microsome transformed with the polynucleotide of the present invention.

An incubation with a yeast microsome and TLC analysis were performed by the same procedure as the above except that the labeled naringenin was used instead of the labeled liquiritigenin as a substrate. As shown in FIG. 7A, P4 (Rf0.69) and P5 (Rf0.64) were confirmed as radioactive spots. Then, the spots of P4 were collected, and treated with HCl. The new spots were obtained as shown in FIG. 7B. These spots showed the same mobility as the sample of genistein. Therefore, it was confirmed that P4 was a 2, 5, 7, 4'-tetra hydroxy isoflavone.

The above-mentioned experiment proved that the protein encoded by CYP Ge-8 acts on both liquiritigenin and naringenin, which may produce 2,7,4'-trihydroxy isoflavanone and 2, 5, 7, 4'-tetrahydroxy isoflavanone, respectively, converting to daidzein and genistein by acid treatment, namely it was IFS. Although dehydration was performed by HCl treatment in the above Example, it is thought that dehydration progresses by the action of a dehydratase in the cell of a licorice.

5. P450 Antisera and Immunoblot Analysis

Consensus amino acid sequences of plant cytochrome P450 have been studied thoroughly, and two oligopeptides shown below were designed as an antigen: (Leu Pro Phe Gly Ser Gly Arg Arg Ser Cys (SEQ ID No.: 6) and Tyr Leu Gln Ala Ile Val Lys Glu Thr Leu Arg Leu (SEQ ID No.: 7)).

The multiple-antigen peptides with N-acetylated amino-terminals synthesized chemically based on these sequences were subcutaneously injected into two rabbits, and the anti-peptide antibody titers in blood were determined with ELISA, and it was revealed that the antibody against P450 was produced. Immunoblotting was conducted using the P450 antisera.

The above yeast microsome was separated on SDS/10% PAGE and transferred onto a Hybond-C membrane (manufactured by Amersham) (about 10 µg protein), and then incubated with a 1:2000 dilution liquid of the P450 antiserum for 1 h at room temperature. The immunoreactive protein was detected by ECL Western blotting analysis system (manufactured by Amersham) according to a manufacturer's protocol.

Figure 8:
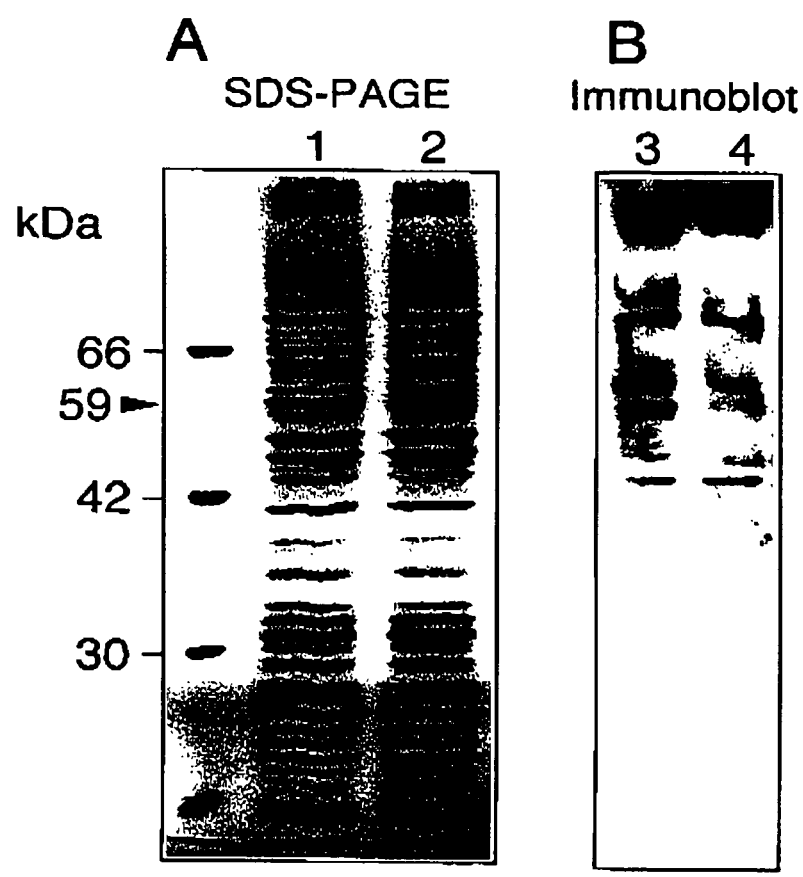
FIG. 8 is a photograph showing the result of SDS/PAGE and immunoblot analysis of a yeast microsome transformed with the polynucleotide of the present invention.

As shown in FIG. 8A, in SDS/PAGE, a new band having a molecular weight of about 59 kDa was detected. It was in agreement with the value (59,428 Da) calculated based on the amino acid sequence.

As shown in FIG. 8B, a prominent signal at 59 kDa was displayed with microsomes of the cells expected to express CYP Ge-8.

6. Northern Blot Analysis

Suspension-cultured cells of licorice cultured under the same culturing conditions as described in the paragraph "1. Plant material and culturing method" were harvested at 3, 6, 12, 24 and 48 h post-elicitation. mRNAs were extracted using Straight A's mRNA Isolation System (manufactured by Novagen). For northern blot analysis, mRNA (900 ng) was subjected to electrophoresis on 1% agarose-formaldehyde gel and transferred onto a Hybond-N+ membrane (manufactured by Amersham). An amount of RNA was determined by staining the gel after electroporation with ethidium bromide. CYP Ge-8 coding region was amplified by PCR using the above-mentioned primers Ge-8 µl and Ge-8A1. Probes for the hybridization were prepared by labelling it by alkaline phosphatase using an AlkPhos Direct system for chemiluminescence (manufactured by Amersham). The blot was hybridized with the probes in the hybridization buffer containing 500 mM NaCl and 4% blocking reagent for 12 h at 55° C. The membranes were washed twice with the primary wash buffer at 55° C. for 10 min and twice with the secondary wash buffer for 5 min at room temperature according to the manufacturer's protocols.

Figure 9:
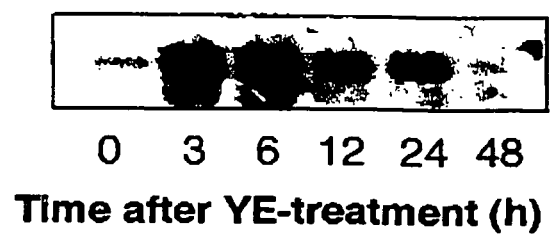
FIG. 9 is a photograph showing the result of a Northern blot analysis of mRNA obtained by the present invention.

As shown in a FIG. 9, it was revealed that there is much accumulation of mRNA in the cell at the time of 3–6-hour progress after elicitor treatment.

7. Introduction of Licorice IFS cDNA into Tobacco Plant a. Construction of a Binary Vector in which IFS is Integrated (Construction of a Vector for Expression in Plants)

Figure 10:
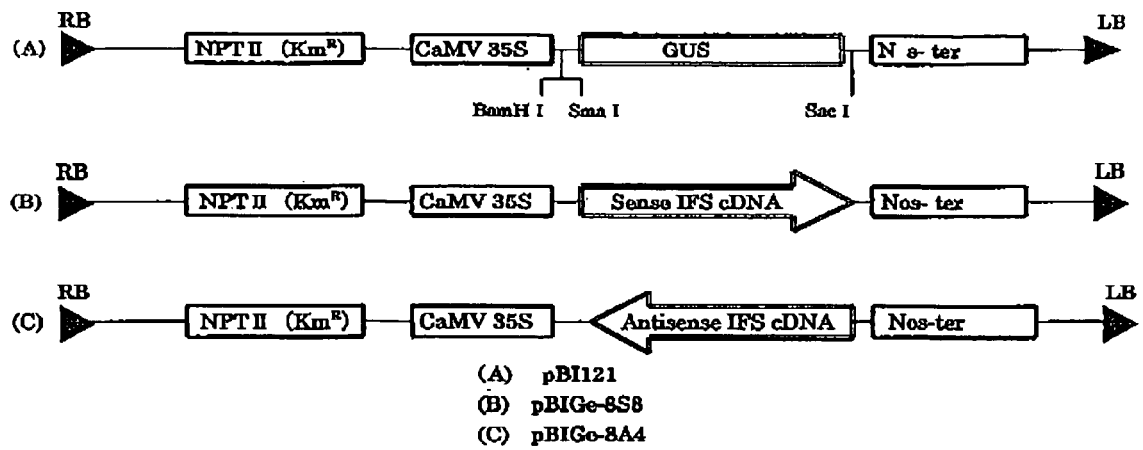
FIG. 10 is an explanatory view showing the binary vector used for the transformation of tobacco which used the polynucleotide of the present invention.

In order to construct the binary vector wherein IFS cDNA was substituted for GUS gene in pBI121 plasmid (see FIG. 10 (A)), the following procedures were conducted.

a-1) Construction of pBI121 from which GUS Gene was Removed (pBI-GUS)

PBI121 plasmid (manufactured by Clontech) was treated with SacI and SmaI (manufactured by TAKARA SHUZO CO., LTD), and the GUS gene was removed. Then, the blunt end was created with T4 DNA polymerase (manufactured by TAKARA SHUZO CO., LTD.), and the vector was self-ligated with DNA Ligation kit ver.2 (manufactured by TAKARA SHUZO CO., LTD.). After that, *Escherichia coli.* DH5α was transformed therewith, and the insertion check of the resultant colony was carried out using pBI12135S, pBI121 Anti primer. As a result, there was obtained pBI-GUS plasmid which was the plasmid having no GUS gene between CaMV35S promoter and Nos-terminator of pBI121 plasmid.

a-2) Creation of IFScDNA Wherein BamHI Sites are Integrated at Both Ends

The primer wherein BamHI sites are integrated at both ends (5'-end, 3'-end) of CDS (coding region) of IFS cDNA and Ge-8S1 (BamHI) primer (SEQ ID No.: 11) and Ge-8AS1 (BamHI) primer (SEQ ID No.: 12) were created.

Ge-8S1 (BamHI) Primer
5'-AAACAGGATCCATGTTGGTGGAACTTG-3'

Ge-8AS1 (BamHI) Primer
5'-GCGCGGGATCCTTACGACGAAAAGAG-3'

PCR was conducted using as a template Ge-8 plasmid (plasmid in which cDNA having the nucleotide sequence of SEQ ID No. 1: was inserted) and using the above-mentioned primers, Ge-8S1 (BamHI) primer and Ge-8AS1 (BamHI) primer. The reaction was performed as follows: one cycle at 98° C. for one minute, 20 cycles of 98° C. for 15 seconds, 55° C. for 10 seconds and 74° C. for 30 seconds, and one cycle at 74° C. for 5 minutes. The KOD polymerase (manufactured by Toyobo Co., Ltd.) was used as DNA polymerase. Thus, IFS cDNA having a BamHI part in 5'-end and 3'-end (both ends) was obtained.

Next, the obtained IFS cDNA was treated with T4 polynucleotide-kinase (manufactured by TAKARA SHUZO CO., LTD.), and the phosphorylation of the 5'-end was carried out. Then, it was subcloned to EcoRV part of pBluescript (manufactured by Stratagene) and confirmed whether the sequence is right by conducting sequencing (or sequence determination), namely whether no variation would occur when amplified with KOD. Sequencing revealed that there was obtained IFS plasmid with no variation and having BamHI sites at 5' and 3'-ends (both ends).

a-3) Ligation of the pBI-GUS Plasmid Created in a-1 and IFScDNA Created in a-2

The pBI-GUS plasmid created in a-1 was treated with BamHI (manufactured by TAKARA SHUZO CO., LTD.), then treated with CIAP (Calf Intestine Alkaline Phosphatase; manufactured by TAKARA SHUZO CO.) and ligated with IFS cDNA having BamHI end at 5'-end and 3'-end which was obtained by treating IFS plasmid (having BamHI sites at both ends) produced in a-2) with BamHI, using DNA ligation kit ver.2 (manufactured by TAKARA SHUZO CO., LTD.), with which *Escherichia coli.* was transformed, and insert check of the resultant colony was conducted (See Fig. (A) to (D)). The following primers were used for the insertion check.

pBI12135S primer (SEQ ID No.: 13) 5'-CTATATAAG-GAAGTTCATTTCATTTGG-3' pBI121 Anti primer (SEQ ID No.: 14) 5'-GACCGGCAA-CAGGATTCAATCTTAAG-3'

Ge-8 S1 primer (SEQ ID No.: 4) 5'-AAACAGGTACCAT-GTTGGTGGAACTTGC-3'

Ge-8 A1 primer (SEQ ID No.: 5) 5'-CGCGCGAATTCTT-TACGACGAAAAGAGTT-3'

Figure 11:
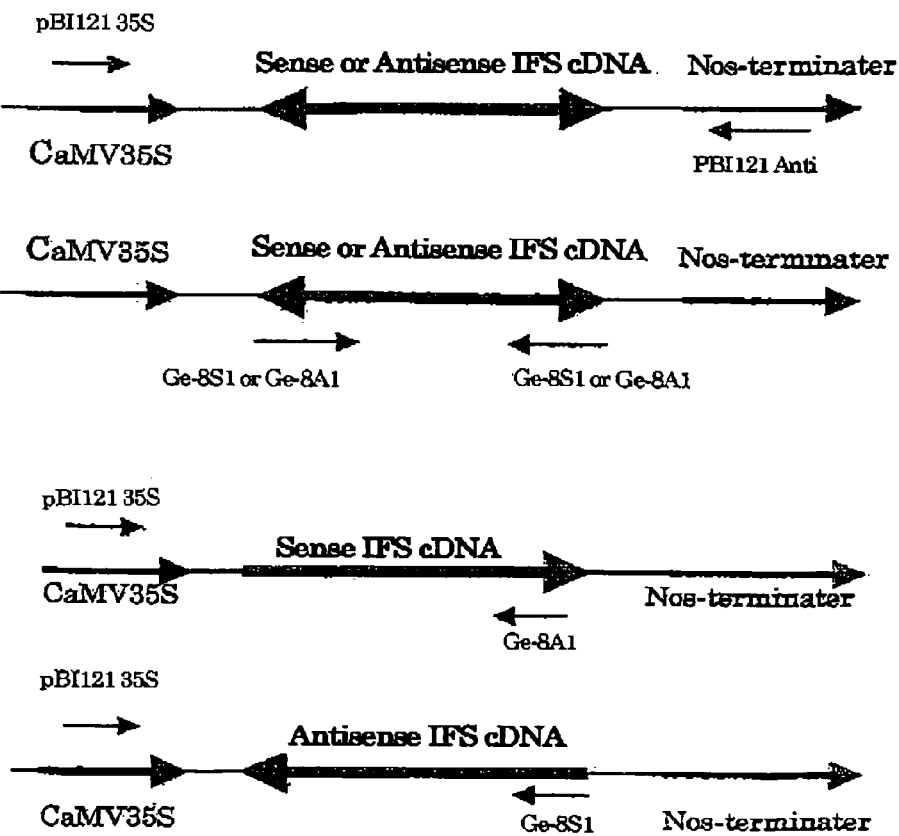
FIG. 11 is a diagram showing the procedure of an insertion check in the transformation of tobacco which used the polynucleotide of the present invention.
Figure 12:
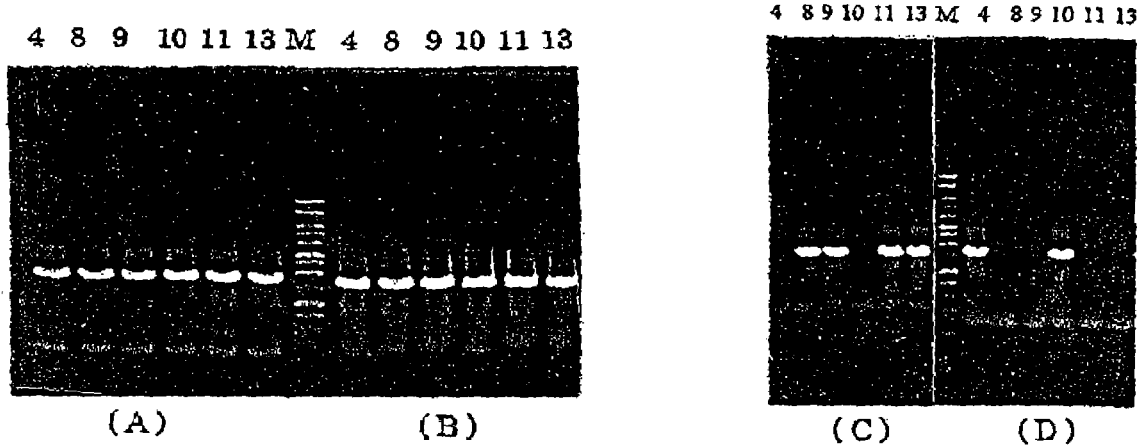
FIG. 12 is a photograph showing the result of the insertion check of FIG. 11.

Consequently, as shown in FIG. 12 (A)–(D), there were obtained four clones (pBIGe-8S8, pBIGe-8S9, pBIGe-8S11, pBIGe-8S13) wherein IFScDNA of the sense direction was introduced into the GUS part of pBI121 (See FIG. 10(B)), and 2 clones wherein IFScDNA of anti sense direction was introduced (pBIGe-8A4 and pBIGe-8A10) (See FIG. 10 (C)). The photographs of (A)–(D) of FIG. 12 show respectively the result of the insertion check shown by (A)–(D) of FIG. 11. In the drawings, pBIGe-8S8, pBIGe-8 S9, pBIGe-8S11, pBIGe-8S13, pBIGe-8A4, and pBIGe-8A10 are referred to, respectively, as 8, 9, 11, 13, 4, and 10.

b. Integration of a Binary Vector to the *Agrobacterium*

The tri-parental mating method (cf. A. Hoekema et al., Nature, 303, 179 (1983); M. Bevan et al., Nucleic Acids Res., 12, 8711 (1984)) was used for integration of the binary vector created by a) into *Agrobacterium*. (the *Eschelichia coli.* HB101 having the helper plasmid pRK2013 was used for providing conjugation-transfer ability.) The binary vector pBIGe-8 S8 (see FIG. 10 (B)) wherein IFS cDNA was inserted in the sense direction, and the binary vector pBIGe-8 A4 (see FIG. 10 (C)) wherein IFS cDNA was inserted in the antisense direction were introduced into *Agrobacterium tumefaciens* LBA4404, respectively.

c. Transformation of Plant (The 1st Day)

c-1) Creation of a Leaf Disk

Two or three leaves were cut from the upper part of tobacco sterile plant (*Nicotiana tabacum* SR1) cultured for about three weeks, and a square leaf disk having a size of 0.5 cm×1 cm was created. The created leaf disk was put on the MS-NB medium, and was cultured under the condition of 25° C. with optical radiation overnight.

c-2) Culturing of an *Agrobacterium*

The two kinds of Agrobacteriums obtained in b) were innoculated in 10 ml of LB+ kanamycin (50 μg/ml) liquid mediums, and cultured with shaking at 28° C. overnight.

(The 2nd Day)

c-3) Infection of *Agrobacterium* to a Leaf Disk and Co-Culturing

The leaf disk created in c-1) was dipped for about 2 minutes in the *Agrobacterium* culture of c-2) cultured overnight. The leaf disk was then taken out, and the excessive culture liquid was wiped with the sterilization paper towel, and put on the medium for co-culturing (where the sterilization filter paper was placed). It was cultured under the condition of 25° C. dark for two days in this state.

(4th Day and After)

c-4) Culturing in the Redifferentiation Medium

The leaf disk was transferred to the redifferentiation medium after the co-culturing for two days, and cultured under the condition of 25° C., dark for 16-hour/light for 8 hours. The leaf disk became callus partially after two to three weeks. The redifferentiation of a shot was observed after further one to two weeks.

The redifferentiated shot was cut out and transferred to the rooting medium.

The followings are compositions of the medium used in the Example:

MS-NB medium: (MS medium, 1 mg/l benzyladenine, 0.1 mg/l naphthalene acetic acid, 3 g/l Gelrite (manufactured by the Wako Pure Chem industry))

co-culturing medium: (MS medium, 3 g/l Gelrite)

redifferentiation medium: (1/2MS medium, 1 mg/l benzyladenine, 0.1 mg/l naphthalene acetic acid, 3 g/l Gelrite, 100 mg/l kanamycin, 400 mg/1 carbenicillin)

rooting medium:

Three weeks at the beginning: (MS medium, 3 g/l Gelrite, a 100 mg/l kanamycin, 200 mg/l carbenicillin)

After three week: (1/2MS medium, 3 g/l Gelrite, 100 mg/l kanamycin, 200 mg/l carbenicillin)

c-6) Check of the Introduced Gene by Genomic PCR

Figure 14:
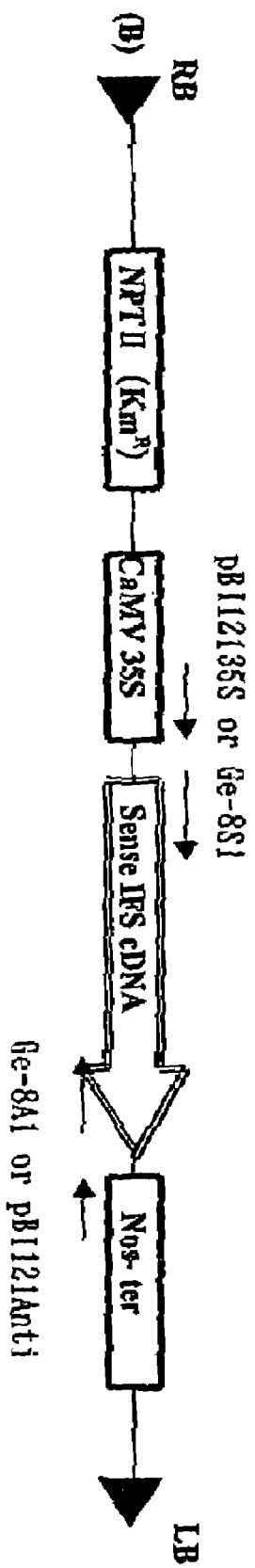
FIG. 14 is an explanatory view showing the procedure of genomic PCR of tobacco transformed using the polynucleotide of the present invention.

As for four stocks (S-1, S-2, S-3, and S-5) in which sense IFS cDNA was introduced among the stocks cultured for about three weeks in rooting medium, genomic PCR was performed as shown in a FIG. 14, and the introduced gene was confirmed. As a control, the tobacco sterile plant in which the gene was not introduced was used.

Two to three leaves were cut from the upper parts of each stock, and DNA was extracted by Dneasy Plant Mini kit (manufactured by QIAGEN).

Using 100 ng of the DNA as a template, PCR of 1 cycle and 95° C. for one minute, then 45 cycles of 95° C. for one minute, 57° C. for one minute and 72° C. for one minute and 30 seconds, and one cycle of 72° C. for five minutes was conducted. Ampli taq Gold™ (manufactured by Perkin-Elmer make) was used as DNA polymerase.

As primers, the primers used for the insertion check in a-1) were used.

Combinations of the used primers are as follows.

(1) Ge-8S1+pBI121Anti
(2) Ge-8S1+Ge-8A1
(3) PBI12135S+pBI121Anti

As for combination of the primers pBI12135S and pBI121Anti of (3), annealing temperature was 50° C.

Figure 13:
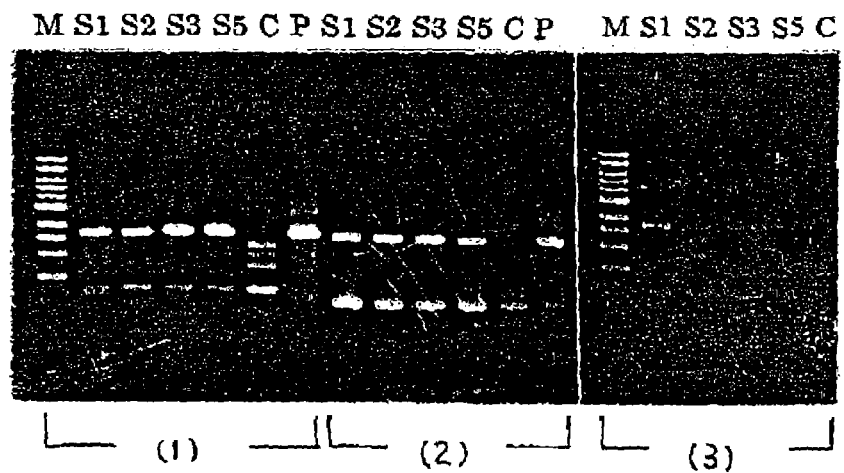
FIG. 13 is a photograph showing the result of genomic PCR of tobacco transformed using the polynucleotide of the present invention.

The result is shown in FIG. 13. FIG. 13 is a photograph showing the result of genomic PCR (1), (2), and (3). The band which is not in a natural tobacco plant (C in the photograph) was seen in all strains S-1, S-2, S-3 and S-5, and it was revealed that IFS cDNA was introduced in the sense direction.

INDUSTRIAL AVAILABILITY

As explained above, the present invention provides a polynucleotide which contains substantially the nucleotide sequence encoding 2-hydroxyisoflavanone synthase. A transformant expressing IFS can be obtained using the polynucleotide. It is useful in production of isoflavones, supply of foods rich in isoflavones, improvement in plant disease resistance, or the like.

---

What is claimed is:

1. An isolated polynucleotide having at least one of (a) a nucleic acid sequence that codes for the protein of SEQ ID NO:2, or (b) the nucleotide sequence complementary to said nucleic acid sequence.

2. A recombinant DNA comprising a polynucleotide of claim 1, which is connected to a regulation sequence that will express the polynucleotide.

3. A method for producing 2-hydroxyisoflavanone synthase comprising culturing a host cell that contains a recombinant DNA according to claim 2.

4. The isolated polynucleotide of claim 1, having at least one of (a) the sequence of nucleotides 144–1712 of SEQ ID NO:1, or (b) the nucleotide sequence complementary thereto.

5. An isolated polynucleotide having at least one of (a) the sequence of SEQ ID NO:1, or (b) the nucleotide sequence complementary thereto.

6. The isolated polynucleotide of claim 1, which codes for SEQ ID NO:2.

7. The polynucleotide of claim 4, having the sequence of nucleotides 144–1712 of SEQ ID NO:1.

8. The polynucleotide of claim 5, having the sequence of SEQ ID NO:1.

9. An isolated polynucleotide comprising at least one of (a) a nucleic acid sequence encoding 2-hydroxyisoflavanone synthase, said nucleic acid sequence having nucleotides 144–1712 of SEQ ID NO:1, or (b) the complement of said nucleic acid sequence.

10. The polynucleotide of claim 9, said nucleic acid sequence having nucleotides 144–1712 of SEQ ID NO:1.

11. A recombinant DNA comprising a polynucleotide of claim 9, which is connected to a regulation sequence that will express the polynucleotide.

12. A method for producing 2-hydroxyisoflavanone synthase comprising culturing a host cell that contains a recombinant DNA according to claim 11.

13. A recombinant DNA comprising a polynucleotide of claim 5, which is connected to a regulation sequence that will express the polynucleotide.

14. A method for producing 2-hydroxyisoflavanone synthase comprising culturing a host cell that contains a recombinant DNA according to claim 13.

* * * * *

SEQUENCE LISTING

<160> NUMBER OF SEQ ID NOS: 14

<210> SEQ ID NO 1
<211> LENGTH: 1895
<212> TYPE: DNA
<213> ORGANISM: Glycyrrhiza echinata
<220> FEATURE:
<221> NAME/KEY: CDS
<222> LOCATION: (144)..(1712)

<400> SEQUENCE: 1

```
cacaaatcct aattgccctc aactcataaa tctctccagg tactggactc ttgttcctgt      60
acttcctcct atactcgact ctttgttatt agttatcatt attattatta caccattaaa     120
gtagcaaaga tcaaacaaac acc atg ttg gtg gaa ctt gca att act ctg ttg    173
                         Met Leu Val Glu Leu Ala Ile Thr Leu Leu
                           1               5                  10 gtg ata gcc ctg ttc ata cac ctg cgt ccc aca cta agt gca aaa tca       221
Val Ile Ala Leu Phe Ile His Leu Arg Pro Thr Leu Ser Ala Lys Ser
         15                  20                  25 aag tcc ctt cgc cac ctc cca aac cct cca agt cca aaa ccc cgt ctc       269
Lys Ser Leu Arg His Leu Pro Asn Pro Pro Ser Pro Lys Pro Arg Leu
     30                  35                  40 cca ttt gtg ggt cac ctt cac ctt tta gac aaa ccc ctt ctc cac tac       317
Pro Phe Val Gly His Leu His Leu Leu Asp Lys Pro Leu Leu His Tyr
 45                  50                  55
```

-continued

| | |
|---|---|
| tcc ctc atc gac cta agc aaa cgc tat ggt ccg ctt tac tcc ctc tac<br>Ser Leu Ile Asp Leu Ser Lys Arg Tyr Gly Pro Leu Tyr Ser Leu Tyr<br>  60                       65                    70 | 365 |
| ttc ggt tcc atg cca acc gtt gta gcc tcc acc cct gaa ctt ttc aaa<br>Phe Gly Ser Met Pro Thr Val Val Ala Ser Thr Pro Glu Leu Phe Lys<br>75                    80                    85                    90 | 413 |
| ctc ttc ctc caa act cac gag gcc tct tcc ttc aac aca agg ttc caa<br>Leu Phe Leu Gln Thr His Glu Ala Ser Ser Phe Asn Thr Arg Phe Gln<br>                    95                          100                  105 | 461 |
| acc tct gcc att agg cgc cta acc tac gac aac tct gtt gcc atg gtt<br>Thr Ser Ala Ile Arg Arg Leu Thr Tyr Asp Asn Ser Val Ala Met Val<br>                110                          115                      120 | 509 |
| ccc ttt ggt cct tac tgg aag ttc att agg aag ctc atc atg aac gac<br>Pro Phe Gly Pro Tyr Trp Lys Phe Ile Arg Lys Leu Ile Met Asn Asp<br>                125                          130                      135 | 557 |
| ctc ctc aat gcc aca act gtg aac aag ttg agg cct tta agg agc caa<br>Leu Leu Asn Ala Thr Thr Val Asn Lys Leu Arg Pro Leu Arg Ser Gln<br>                140                          145                      150 | 605 |
| gaa atc cga aag gtc ctc agg gtg atg gca cag agt gct gag tct cag<br>Glu Ile Arg Lys Val Leu Arg Val Met Ala Gln Ser Ala Glu Ser Gln<br>155                    160                    165                    170 | 653 |
| gtc cca ctt aat gtc acc gag gag ctt ctc aag tgg acc aac agc acc<br>Val Pro Leu Asn Val Thr Glu Glu Leu Leu Lys Trp Thr Asn Ser Thr<br>                    175                          180                  185 | 701 |
| atc tcg agg atg atg ctt ggg gaa gca gag gaa atc agg gac ata gca<br>Ile Ser Arg Met Met Leu Gly Glu Ala Glu Glu Ile Arg Asp Ile Ala<br>                190                          195                    200 | 749 |
| cgt gac gtg ctt aag atc ttt ggg gag tat agt ctc acc gac ttc atc<br>Arg Asp Val Leu Lys Ile Phe Gly Glu Tyr Ser Leu Thr Asp Phe Ile<br>                205                          210                    215 | 797 |
| tgg ccc ttg aag aaa ctc aag gtt ggg caa tac gag aag agg att gac<br>Trp Pro Leu Lys Lys Leu Lys Val Gly Gln Tyr Glu Lys Arg Ile Asp<br>220                    225                    230 | 845 |
| gat ata ttc aac agg ttt gac ccc gtc att gag agg gtc atc aag aaa<br>Asp Ile Phe Asn Arg Phe Asp Pro Val Ile Glu Arg Val Ile Lys Lys<br>235                    240                    245                    250 | 893 |
| aga cag gag att agg aag aag agg aag gag agg aat ggt gag atc gag<br>Arg Gln Glu Ile Arg Lys Lys Arg Lys Glu Arg Asn Gly Glu Ile Glu<br>                255                          260                    265 | 941 |
| gag ggt gaa cag agt gtg gtt ttt ctc gac act ttg ctc gat ttt gct<br>Glu Gly Glu Gln Ser Val Val Phe Leu Asp Thr Leu Leu Asp Phe Ala<br>                    270                          275                    280 | 989 |
| gag gac gag acc atg gag atc aaa atc acc aag gaa caa atc aag ggc<br>Glu Asp Glu Thr Met Glu Ile Lys Ile Thr Lys Glu Gln Ile Lys Gly<br>                285                          290                    295 | 1037 |
| ctt gtt gtg gat ttc ttc tca gca ggg acg gat tcc acg gcg gtg gca<br>Leu Val Val Asp Phe Phe Ser Ala Gly Thr Asp Ser Thr Ala Val Ala<br>                300                          305                    310 | 1085 |
| aca gac tgg gct ctg tca gag ctc atc aac aac ccc agg gtg ttt caa<br>Thr Asp Trp Ala Leu Ser Glu Leu Ile Asn Asn Pro Arg Val Phe Gln<br>315                      320                    325                    330 | 1133 |
| aag gca cga gag gag atc gat gcc gtc gtg gga aaa gac aga ctc gtt<br>Lys Ala Arg Glu Glu Ile Asp Ala Val Val Gly Lys Asp Arg Leu Val<br>                335                          340                    345 | 1181 |
| gac gag gca gat gtc cag aac ctt cct tac att aga tcc atc gtg aag<br>Asp Glu Ala Asp Val Gln Asn Leu Pro Tyr Ile Arg Ser Ile Val Lys<br>                    350                          355                    360 | 1229 |
| gag acg ttc cgc atg cac cca cca cta ccc gtg gtc aaa aga aag tgc<br>Glu Thr Phe Arg Met His Pro Pro Leu Pro Val Val Lys Arg Lys Cys | 1277 |

-continued

```
                  365                 370                 375
gtg cag gag tgt gag gtc gac ggt tat gtg atc cca gag gga gca ttg      1325
Val Gln Glu Cys Glu Val Asp Gly Tyr Val Ile Pro Glu Gly Ala Leu
        380                 385                 390 atc ctt ttc aat gtt tgg gcc gtc gga aga gac cca aaa tac tgg gac      1373
Ile Leu Phe Asn Val Trp Ala Val Gly Arg Asp Pro Lys Tyr Trp Asp
395                 400                 405                 410 agg ccc act gag ttc cgt ccc gaa agg ttc tta gaa aat gtg ggt gaa      1421
Arg Pro Thr Glu Phe Arg Pro Glu Arg Phe Leu Glu Asn Val Gly Glu
                415                 420                 425 ggg gat caa gcc gtt gac ctt agg ggt caa cat ttc caa ctt ctt ccg      1469
Gly Asp Gln Ala Val Asp Leu Arg Gly Gln His Phe Gln Leu Leu Pro
        430                 435                 440 ttt ggg tct gga agg agg atg tgc cct ggc gtc aat ttg gcc act gcg      1517
Phe Gly Ser Gly Arg Arg Met Cys Pro Gly Val Asn Leu Ala Thr Ala
445                 450                 455 gga atg gcc aca ctg ctt gcg tca gtt atc cag tgc ttt gat ctc agc      1565
Gly Met Ala Thr Leu Leu Ala Ser Val Ile Gln Cys Phe Asp Leu Ser
    460                 465                 470 gta gtg ggc cca cag gga aag ata ttg aag ggc aat gat gcc aag gtt      1613
Val Val Gly Pro Gln Gly Lys Ile Leu Lys Gly Asn Asp Ala Lys Val
475                 480                 485                 490 agc atg gaa gag aga gct gga ctc acg gtt cca agg gca cat aac ctc      1661
Ser Met Glu Glu Arg Ala Gly Leu Thr Val Pro Arg Ala His Asn Leu
                495                 500                 505 atc tgt gtc ccg gtt gca aga tca agt gcc gta ccc aaa ctc ttt tcg      1709
Ile Cys Val Pro Val Ala Arg Ser Ser Ala Val Pro Lys Leu Phe Ser
        510                 515                 520 tcg taaaacatac gcgcgacacc agaaagctgc catggcatga tgctttttat           1762
Ser ataataattt tcaataaggt atcaatcaat gatatataga caatgatacc catatatcat    1822
cttcgcgact agtctctctt tggtacagta tgttgtaaca gcttaaatct atataatttt    1882
tactcgcata tcc                                                       1895
```

<210> SEQ ID NO 2
<211> LENGTH: 523
<212> TYPE: PRT
<213> ORGANISM: Glycyrrhiza echinata

<400> SEQUENCE: 2

```
Met Leu Val Glu Leu Ala Ile Thr Leu Leu Val Ile Ala Leu Phe Ile
1               5                   10                  15

His Leu Arg Pro Thr Leu Ser Ala Lys Ser Lys Ser Leu Arg His Leu
            20                  25                  30

Pro Asn Pro Pro Ser Pro Lys Pro Arg Leu Pro Phe Val Gly His Leu
        35                  40                  45

His Leu Leu Asp Lys Pro Leu Leu His Tyr Ser Leu Ile Asp Leu Ser
    50                  55                  60

Lys Arg Tyr Gly Pro Leu Tyr Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Ser Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125
```

-continued

Lys Phe Ile Arg Lys Leu Ile Met Asn Asp Leu Leu Asn Ala Thr Thr
130                 135                 140

Val Asn Lys Leu Arg Pro Leu Arg Ser Gln Glu Ile Arg Lys Val Leu
145                 150                 155                 160

Arg Val Met Ala Gln Ser Ala Glu Ser Gln Val Pro Leu Asn Val Thr
            165                 170                 175

Glu Glu Leu Leu Lys Trp Thr Asn Ser Thr Ile Ser Arg Met Met Leu
            180                 185                 190

Gly Glu Ala Glu Glu Ile Arg Asp Ile Ala Arg Asp Val Leu Lys Ile
            195                 200                 205

Phe Gly Glu Tyr Ser Leu Thr Asp Phe Ile Trp Pro Leu Lys Lys Leu
210                 215                 220

Lys Val Gly Gln Tyr Glu Lys Arg Ile Asp Asp Ile Phe Asn Arg Phe
225                 230                 235                 240

Asp Pro Val Ile Glu Arg Val Ile Lys Lys Arg Gln Glu Ile Arg Lys
                245                 250                 255

Lys Arg Lys Glu Arg Asn Gly Glu Ile Glu Glu Gly Glu Gln Ser Val
            260                 265                 270

Val Phe Leu Asp Thr Leu Leu Asp Phe Ala Glu Asp Thr Met Glu
            275                 280                 285

Ile Lys Ile Thr Lys Glu Gln Ile Lys Gly Leu Val Val Asp Phe Phe
290                 295                 300

Ser Ala Gly Thr Asp Ser Thr Ala Val Ala Thr Asp Trp Ala Leu Ser
305                 310                 315                 320

Glu Leu Ile Asn Asn Pro Arg Val Phe Gln Lys Ala Arg Glu Glu Ile
                325                 330                 335

Asp Ala Val Val Gly Lys Asp Arg Leu Val Asp Glu Ala Asp Val Gln
            340                 345                 350

Asn Leu Pro Tyr Ile Arg Ser Ile Val Lys Glu Thr Phe Arg Met His
            355                 360                 365

Pro Pro Leu Pro Val Val Lys Arg Cys Val Gln Glu Cys Glu Val
370                 375                 380

Asp Gly Tyr Val Ile Pro Glu Gly Ala Leu Ile Leu Phe Asn Val Trp
385                 390                 395                 400

Ala Val Gly Arg Asp Pro Lys Tyr Trp Asp Arg Pro Thr Glu Phe Arg
                405                 410                 415

Pro Glu Arg Phe Leu Glu Asn Val Gly Glu Gly Asp Gln Ala Val Asp
            420                 425                 430

Leu Arg Gly Gln His Phe Gln Leu Leu Pro Phe Gly Ser Gly Arg Arg
            435                 440                 445

Met Cys Pro Gly Val Asn Leu Ala Thr Ala Gly Met Ala Thr Leu Leu
450                 455                 460

Ala Ser Val Ile Gln Cys Phe Asp Leu Ser Val Val Gly Pro Gln Gly
465                 470                 475                 480

Lys Ile Leu Lys Gly Asn Asp Ala Lys Val Ser Met Glu Glu Arg Ala
                485                 490                 495

Gly Leu Thr Val Pro Arg Ala His Asn Leu Ile Cys Val Pro Val Ala
            500                 505                 510

Arg Ser Ser Ala Val Pro Lys Leu Phe Ser Ser
            515                 520

<210> SEQ ID NO 3
<211> LENGTH: 422
<212> TYPE: DNA

-continued

<213> ORGANISM: Glycyrrhiza echinata

<400> SEQUENCE: 3

```
gatgtgccct ggcgtgaatt tggccactgc ggggatggcc acactgcttg cgtcagttat    60
ccagtgcttt gatctcagcg tagtgggccc acagggaaag atattgaagg gcaatgatgc   120
caaggttagc atggaagaga gagctggact cacggttcca agggcacata acctcatctg   180
tgtcccggtt gcaagatcaa gtgccgtacc caaactcttt tcgtcgtaaa acatacgcgc   240
gacaccacag aaagttgcca tggcatgatg ctttttatat aataattttc aataaggtat   300
caatcaatga tatatagaca atgataccca tatatcatct tcacgactag tctctctttg   360
gtacagtatg ttgtaacagc ttaaatctat ataattttta ctcgcatatc catttcctga   420
tt                                                                  422
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4

```
aaacaggtac catgttggtg gaacttgc                                       28
```

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5

```
cgcgcgaatt ctttacgacg aaaagagtt                                      29
```

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Primer

<400> SEQUENCE: 6

Leu Pro Phe Gly Ser Gly Arg Arg Ser Cys
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Primer

<400> SEQUENCE: 7

Tyr Leu Gln Ala Ile Val Lys Glu Thr Leu Arg Leu
  1               5                  10

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base

```
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)..(15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i

<400> SEQUENCE: 8
htnscnttyr gnnnnggnms nmg                                          23

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
aatacgactc actatag                                                 17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 10
attaaccctc actaaag                                                 17

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
aaacaggatc catgttggtg gaacttg                                      27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
gcgcgggatc cttacgacga aaagag                                       26

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer
```

```
<400> SEQUENCE: 13
ctatataagg aagttcattt catttgg                                              27

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
gaccggcaac aggattcaat cttaag                                               26
```